United States Patent
Sović et al.

(10) Patent No.: US 11,821,031 B2
(45) Date of Patent: Nov. 21, 2023

(54) SYSTEMS AND METHODS FOR GRAPH BASED MAPPING OF NUCLEIC ACID FRAGMENTS

(71) Applicant: Pacific Biosciences of California, Inc., Menlo Park, CA (US)

(72) Inventors: Ivan Sović, Ivanić-Grad (HR); James Drake, San Jose, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 805 days.

(21) Appl. No.: 16/752,111

(22) Filed: Jan. 24, 2020

(65) Prior Publication Data

US 2020/0239949 A1    Jul. 30, 2020

Related U.S. Application Data

(60) Provisional application No. 62/797,022, filed on Jan. 25, 2019.

(51) Int. Cl.
     *C12Q 1/6869*     (2018.01)
     *G06N 3/123*      (2023.01)
     *G06N 3/126*      (2023.01)

(52) U.S. Cl.
     CPC .......... *C12Q 1/6869* (2013.01); *G06N 3/123* (2013.01); *G06N 3/126* (2013.01); *C12Q 2535/122* (2013.01)

(58) Field of Classification Search
     CPC ........... C12Q 1/6869; C12Q 2535/122; C06N 3/123; C06N 3/126
See application file for complete search history.

(56) References Cited

U.S. PATENT DOCUMENTS

| 11,319,595 B2 * | 5/2022 | Babiarz ................. G16B 20/00 |
| 2013/0124100 A1 * | 5/2013 | Drmanac ............... G16B 30/10 |
| | | 702/20 |

(Continued)

OTHER PUBLICATIONS

Weisenfeld NI, Kumar V, Shah P, Church DM, Jaffe DB. Direct determination of diploid genome sequences. Genome Res. May 2017;27(5):757-767. doi: 10.1101/gr.214874.116. Epub Apr. 5, 2017. Erratum in: Genome Res. Apr. 2018;28(4):606.1. PMID: 28381613; PMCID: PMC5411770. (Year: 2018).*

(Continued)

*Primary Examiner* — Raymond L Nimox
(74) *Attorney, Agent, or Firm* — Morgan, Lewis & Bockius LLP

(57) ABSTRACT

Technical solutions for mapping long nucleic acid sequence reads to a target sequence are provided. A directed graph, representing all or some of a genome and comprising one or more nonlinear topological components, is obtained for an organism having a heterozygous genome. Each nonlinear topological component has an initiating node and a terminal node connected by at least a first branch and a second branch. One of these branches corresponds to the target sequence. The directed graph uses a plurality of sequence reads from a biological sample of the organism. The sequence reads are overlapped by an unrestricted overhang amount, provided there is a minimum consensus region between each two sequence reads. A query sequence, encompassing at least the initiating node or the terminal node of a first nonlinear topological component, is obtained. The directed graph is used to form a mapping of the query sequence to the directed graph.

13 Claims, 8 Drawing Sheets

(56) References Cited

U.S. PATENT DOCUMENTS

| | | | | |
|---|---|---|---|---|
| 2014/0025312 A1* | 1/2014 | Chin | ............... | G16B 30/20 |
| | | | | 702/20 |
| 2015/0169823 A1* | 6/2015 | Chin | ............... | G16B 5/00 |
| | | | | 702/20 |
| 2015/0286775 A1* | 10/2015 | Chin | ............... | G16B 30/20 |
| | | | | 702/20 |
| 2016/0246922 A1* | 8/2016 | Putnam | ............... | G16B 30/00 |
| 2016/0350478 A1* | 12/2016 | Chin | ............... | G16B 20/00 |
| 2017/0058365 A1* | 3/2017 | Locke | ............... | G16B 30/00 |
| 2017/0109383 A1* | 4/2017 | Semenyuk | ............... | G16B 50/20 |
| 2019/0244678 A1* | 8/2019 | Konvicka | ............... | G16B 20/20 |

OTHER PUBLICATIONS

K. Meltz Steinberg et al., "Building and Improving Reference Genome Assemblies," in Proceedings of the IEEE, vol. 105, No. 3, pp. 422-435, Mar. 2017, doi: 10.1109/JPROC.2016.2645402. (Year: 2017).*

Leggett RM, MacLean D. Reference-free SNP detection: dealing with the data deluge. BMC Genomics. 2014;15 Suppl 4(Suppl 4): S10. doi: 10.1186/1471-2164-15-S4-S10. Epub May 20, 2014. PMID: 25056481; PMCID: PMC4083407. (Year: 2014).*

Myers, Eugene W., "The Fragment Assembly String Graph", Bioinformatics, v. 21, suppl. 2 2005, p. ii79-ii85.

Altschul, S., et al., "Basic Local Alignment Search Tool", J Mol Biol 215:403-410 (1990).

Chaisson et al., "*Mapping Single Molecule Sequencing Reads Using Basic Local Alignment with Successive Refinement (BLASR): Application and Theory*" BMC Bioinformatics 13:238, 2012.

Chen, K. et al., "BreakDancer: an Algorithm for High-Resolution Mapping of Genomic Structural Variation", Nat Methods 6(9):677-681, (2009).

Chin, C-S, et al., "Phased Diploid Genome Assembly with Single Molecule Real-Time Sequencing", Nat Methods 13(12):1050-1054 (2016).

Chin, C-S, et al., "Nonhybrid, Finish Microbial Genome Assemblies from Long-Read SMRT Sequencing Data", Nat Methods 10(6):563-569 (2013).

Choi et al., "Comparison of Phasing Strategies for Whole Human Genomes", PLOS Genetics 14(4) (2018).

Clark, J. et al., "Genome Evolution of Ferns: Evidence for Relative Stasis of Genome Size Across the Fern Phylogeny", New Phytologist, 210:1072-82 (2016).

Compeau, et al., "Why are de Bruijn Graphs Useful for Genome Assembly?", Nat Biotechnol 29(11):987-991, (2011).

Daily, J. "Parasail: SIMD C Library for Global, Semi-Global, and Local Pairwise Sequence Alignments", BMC Bioinformatics 17:81, (2016).

Garrison et al., "Variation Graph Toolkit Improves Read Mapping by Representing Genetic Variation in the Reference", Nat. Biotech. 36(9), 875-879, 2018.

Ghodsi et al., "DNAClust: Accurate and Efficient Clustering of Phylogenetic Marker Genes", BMC Bioinformatics 12:271 (2011).

Ghurye et al., "*Integrating Hi—C Links with Assembly Graphs for Chromosome-Scale Assembly*" bioRxiv 261149; on the Internet at doi.org/10.1101/261149.

Jayakumar, V. et al. "Comprehensive Evaluation of Non-Hybrid Genome Assembly Tools for Third-Generation PacBio Long-Read Sequence Data", Briefings in Bioinformatics, 2017, 1-11.

Jiang, H. et al., "Skewer: a Fast and Accurate Adapter Trimmer for Next-Generation Sequencing Paired-End Reads", BMC Bioinformatics 15:182 (2014).

Kavya et al., "Sequence Allignment on Directed Graphs", J Comp Biol 26:1-15 (2019).

Kelly M.J., "Computers: the Best Friends a Human Genome Ever Had", Genome, 31(2):1027-33 (1989).

Langmead, B. et al., "Fast Gapped-Read Alignment with bowtie 2", Nat Methods 9(4):357-359, (2012).

Li, H., "Minimap2: Pairwise Alignment for Nucleotide Sequences", Bioinformatics; 34(18):3094-3100, (2018).

Li, H., et al., "Fast and Accurate Long-Read Alignment with Burrows-Wheeler Transform", Bioinformatics 26(5):589-595, (2010).

Li, H. et al., "A Survey of Sequence Alignment Algorithms for Next-Generation Sequencing", Briefings in Bioinformatics 11(5):473-483, (2010).

Li, H. et al., "Mapping Short DNA Sequencing Reads and Calling Variants Using Mapping Quality Scores", Genome Res 18(11):1851-1858 (2008).

Limasset et al., , "Read Mapping on deBruijn Graphs", BMC Bioinformatics 17:237 (2016).

Liu, B., et al., "deBGA: Read Alignment with de Bruijn Graph-Based Seed Extension", Bioinformatics 32(21):3224-3232 (2016).

Maciuca, S. et al., "A Natural Encoing of Genetic Variation in a Burrows-Wheeler Transform to Enable Mapping and Genome Inference", 2016, on the Internet at dx.doi.org/10.1101/059170.

Makoff A.J., et al, "Detailed Analysis of I 5ql 1-q I 4 Sequence Corrects Errors and Gaps in the Public Access Sequence to Fully Reveal Large Segmental Duplications at Breakpoints for Prader-Willi, Angelman, and Inv Dup(I 5) Syndromes", Genome Bio 8(6):R114 (2007).

Pollard, M. et al., "Long Reads: Their Purpose and Place", Hum Molecul Genetics, v. 27, n. R2, p. R234-R241 (2018).

Rhoads, A., et al., "PacBio Sequencing and its Applications", Genomics Proteomics Bioinformatics 13:278-289, (2015).

Rizk, G., et al., "GASSST: Global Alignment Shor Sequence Search Tool", Bioinformatics 26(20):2534-2540 (2010).

Ruffalo, M. et al., "Accurate Estimation of Short Read Mapping Quality for Next-Generation Genome Sequencing", Bioinformatics 28(5):i349-i355 (2012).

Schbath, S., et al., "Mapping Reads on a Genomic Sequence: An Algorithmic Overview and a Practical Comparative Analysis", J. Comp. Biol., v. 19, n.6, p. 796-813, 2012.

Sirén et al., "Indexing Variation Graphs", Proc. ALENEX 2017, SIAM, pp. 13-27, DOI: 10.1137/1.9781611974768.2.

Smith, et al., "Identification of Common Molecular Subsequences", J Mol Biol 147(1):195-197 (1981).

Sović et al., "Fast and Sensitive Mapping of Nanopore Sequencing Reads wit GraphMap", Nat Comm 7:11307 (2016).

Spielmann M., et al., "Structural Variation in the 3D Genome", Nat Rev Genetics 19:453-467 (2018).

Travers et al., "A Flexible and Efficient Template Format for Circular Consensus Sequencing and SNP Detection", Nucleic Acids Res 38(15):e159, 2010.

Vollmers, J. et al., "Comparing and Evaluating Metagenome Assembly Tools from a Microbiologist's Perspective—Not Only Size Matters!", PLoS One 12(1) (2017).

Ye, Y. et al., "BlastGraph: a Comparative Genomics Tool Based on BLAST and Graph Algorithms", Bioinformatics 29(24):3222-3224, 2013.

* cited by examiner

```
┌─────────────────────────────────────┐
│ A nucleic acid sequencing method.   │─── 202
└─────────────────────────────────────┘
                  │
                  ▼                                              ─── 204
┌──────────────────────────────────────────────────────────────────┐
│ Obtain a directed graph for a single diploid or polyploid organism of a species having a │
│ heterozygous genome, where the directed graph represents all or a portion of the heterozygous │
│ genome and comprises one or more nonlinear topological components, where each respective │
│ nonlinear topological component in the one or more nonlinear topological components represents │
│ a variation with respect to a set of target sequences.                                       │─── 206
│  ┌─────────────────────────────────────────────────────────────┐ │
│  │ The directed graph represents at least ten percent of the heterozygous genome, and the directed │ │
│  │ graph comprises ten or more nonlinear topological components. │ │
│  └─────────────────────────────────────────────────────────────┘ │─── 208
│  ┌─────────────────────────────────────────────────────────────┐ │
│  │ The directed graph represents at least fifty percent of the heterozygous genome, and the │ │
│  │ directed graph comprises twenty-five or more nonlinear topological components. │ │
│  └─────────────────────────────────────────────────────────────┘ │─── 210
│ ┌──────────────────────────────────────────────────────────────┐ │
│ │ Each respective nonlinear topological component in the one or more nonlinear topological │ │
│ │ components has a corresponding initiating node and a corresponding terminal node that is │ │
│ │ connected by at least a corresponding first branch and a corresponding second branch, where │ │
│ │ one of the corresponding first branch and the corresponding second branch corresponds to the │ │
│ │ target sequence.                                              │ │─── 212
│ │  ┌─────────────────────────────────────────────────────────┐ │ │
│ │  │ The corresponding first and second branch of a nonlinear topological component in the │ │ │
│ │  │ one or more nonlinear topological components respectively represent a first allele and a │ │ │
│ │  │ second allele for a variation in the heterozygous genome │ │ │
│ │  └─────────────────────────────────────────────────────────┘ │ │─── 214
│ ┌──────────────────────────────────────────────────────────────┐ │
│ │ The directed graph is formed using a plurality of sequence reads from a biological sample of │ │
│ │ the single organism, which collectively have random error with respect to the target sequence │ │
│ │ that is greater than ten percent, by overlapping respective sequence reads in the plurality of │ │
│ │ sequence reads, where an amount of overhang between an overlapped first sequence read and │ │
│ │ second sequence is unrestricted provided there is a minimum consensus region between the │ │
│ │ first and second sequence reads.                             │ │─── 216
│ │  ┌─────────────────────────────────────────────────────────┐ │ │
│ │  │ The plurality of sequence reads has an average sequence length of greater than 10,000 │ │ │
│ │  │ base pairs.                                              │ │ │
│ │  └─────────────────────────────────────────────────────────┘ │ │
│ └──────────────────────────────────────────────────────────────┘ │
└──────────────────────────────────────────────────────────────────┘
                                 │
                                 ▼
```

Figure 2A

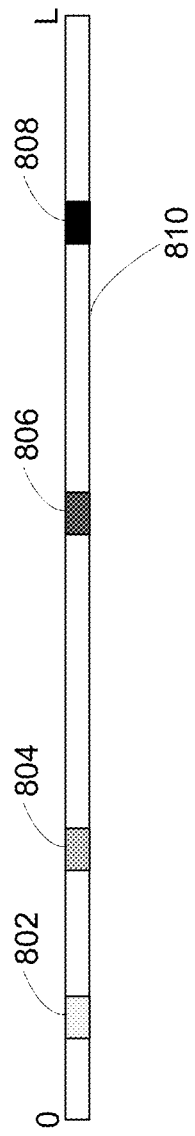
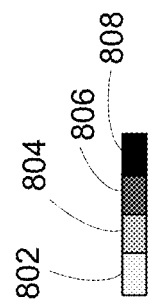
Figure 8A
Figure 8B

SYSTEMS AND METHODS FOR GRAPH BASED MAPPING OF NUCLEIC ACID FRAGMENTS

CROSS REFERENCE TO RELATED APPLICATION

This application claims priority to U.S. Provisional Patent Application No. 62/797,022, filed Jan. 25, 2019, the disclosure of which is hereby incorporated by reference herein in its entirety for all purposes.

TECHNICAL FIELD

This specification describes using graph based mapping to combine nucleic acid fragments into a coherent sequence.

BACKGROUND

Advances in biomolecule sequencing, in particular with respect to nucleic acid and protein samples, have revolutionized the fields of cellular and molecular biology. Facilitated by the development of automated sequencing systems, it is now possible to sequence whole genomes. However, there has also been a commensurate increase in the number and complexity of the genomes that are being sequenced with these new sequencing technologies. Although large quantities of high-fidelity nucleic acid sequences can now be obtained, there remain many issues with assembling and organizing these sequences into complete genomes.

Assembly of these complex genomes, particularly diploid and higher-ploidy genomes, from sequence reads is a difficult problem that is necessarily rooted in computing technology. This is due to multiple factors, including the sheer size of genomes, read-size limitations of conventional sequencing technologies, and sequence variations in homologous regions of polyploidy genomes. For instance, while the relatively 'simple' monoploid genome of *Escherichia coli* only includes 4.6 million base pairs in a single circular genome, the human genome includes two copies of twenty-three chromosomes, each copy containing over 3.2 billion base pairs.

Assuming an average sequencing read length of 250 base pairs and an average overlap of only 15% between sequence reads, nearly 30 million sequence reads would be needed for 1× coverage of the human genome. Further, the human genome includes two copies of each locus, the sequences of which vary by approximately 0.1%, meaning that over 22% of 250 base pair sequence reads will diverge from any particular reference genome used to assist the assembly process. Moreover, the 22% of sequence reads that diverge, representing approximately 6.5 million sequence reads, need to be phased relative to each other, in order to assemble haplotigs for the diploid genome. This is only further complicated in high-order polyploidy genomes such as ferns (mean 2n=121.0; 2n range=18-1440; Clark J et al., New Phytologist, 210:1072-82 (2016)). Accordingly, it is clear that genome assembly cannot practically be performed without using computing technology. See, Kelly M J. Computers: the best friends a human genome ever had, Genome, 31(2):1027-33 (1989).

However, the mere computing power of general purpose computers is not all that is required for efficient genome assembly, as is evidenced by the extensive effort required of the human genome project, even with the aid of computing technologies (13 years to complete with worldwide cooperation; Chial, H., DNA sequencing technologies key to the Human Genome Project, Nature Education, 1(1):219 (2008)). Rather, complex alignment algorithms are needed to process the extremely large amount of sequencing data required of genome assembly. The development of more greedy alignment algorithms have drastically sped-up genome assembly processes, relative to the first human genome assembled.

Mapping sequencing reads is embodied in tools ranging from BLAST, to BLASR, BWA-MEM, DAMAPPER, NGMLR, GraphMap, Minimap, among others. Each of these methods have their own particular requirements and uses. However, all of them share a common design for mapping to linear target sequences such as reference genomes. On the other hand, mappers such as BGREAT (as described in Limasset et al., 2016, BMC Bioinformatics 17:237) and deBGA (e.g., as described by Liu et al., 2016, Bioinformatics 32(21):3224-3232) are designed to work with both second generation sequencing data and de Bruijn graphs as opposed to linear target sequences. BlastGraph uses BLAST mapping results to cluster alignments and perform comparative genomic analyses (as described in Ye et al., 2013, Bioinformatics 29(24):3222-3224). However, according to experiments performed by Limasset et al., BlastGraph does not perform well on even simple non-linear datasets such as the *Escherichia coli* genome (BMC Bioinformatics 17:237, 2016). GramTools maps short reads to a population reference graph (e.g., as described in Maciuca et al., 2016, on the Internet at dx.doi.org/10.1101/059170). In general, all of these methods are specifically designed to perform with short-read sequences.

While useful for assembling relatively simple linear genomic regions, there are many disadvantages to short-read sequences. For example, short-read sequences provide limited information in genomic regions with high GC content, in repetitive regions, and in regions exhibiting structural variations such as duplications (e.g., in Pollard et al., 2018, Hum Molecul Genetics 27(R2):R234-R241). Mappers capable of accurately and efficiently using long-read sequences will become ever more necessary, as more complex genomes are sequenced and assembled. One method currently capable of mapping long noisy reads to an arbitrary sequence graph is the variation graph (e.g., "vg") toolkit, which provides tools to construct, view and manipulate the variation graphs, including features such as full-length POA alignment on the graph, mapping reads and calling variants from read alignments (e.g., as described in Garrison et al., 2018, Nat. Biotech. 36, 875-879). It was originally designed and optimized for short reads, and later modified to support longer sequences by splitting them into short overlapping chunks (essentially emulating short reads). However, to implement the graph-based functionality vg uses a BWT-based indexing approach for directed graphs (GCSA2), which indexes paths only up to length 256 in any graph (e.g., as described in Sirén et al., Proc. ALENEX 2017, SIAM, pp. 13-27, Barcelona, Spain, Jan. 17-18, 2017. DOI: 10.1137/1.9781611974768.2). The upper bound on path length is intended as a heuristic to prevent "combinatorial explosion" in regions with a lot of branching. Vg also unrolls and unfolds the cyclic directed graphs to make directed acyclic graphs (process of "DAGification") on which the partial order alignment can be applied (e.g., in Garrison et al., 2018, Nat. Biotech. 36, 875-879). Unrolling cycles in the graph is also an expensive combinatorial operation which can drastically increase the size of the graph (e.g., as described in Kavya et al., 2019, J Comp Biol 26:1-15 and Naga et al., 2019, J Comp Biol 26(1)). Further, although the GCSA2 indexing approach provides linear-time exact-match queries independent of the graph size to find super maximal exact matching seeds, BWT and FM-index based algorithms in general may carry a large hidden constant factor during lookup as well as significant time required to pre-build the index, which needs to be taken into account when considering the maximum mapping rate to large sequences and graphs. Therefore, while vg's paradigm is well suited for many applications, there are many other types of genomes that require different methods.

One example of a use case for graph-based mapping is in the context of a circular type of genome. When faced with sequences from a circular genome, most mappers either demonstrate a significant drop in coverage near the ends of the reference circular sequence (e.g. BLASR, as described by Chaisson and Tesler BMC Bioinformatics 13:238, 2012), or maintain high sequencing coverage by outputting supplementary alignments which are not directly tied to the primary alignment (they could also be placed in repeat regions) (e.g., Minimap2, as described by Li, Bioinformatics 15; 34(18):3094-3100, 2018). One method of overcoming this deficiency is to use a graph-based mapping method. Defining references as graphs enables seemingly transparent support for a wide range of important applications. Indeed, Minimap2 and GraphMap do seek to address the circular-genome mapping problem (e.g., see Id. and Sović et al., 2016, Nat Comm 7:11307). However, a significant limitation of GraphMap in particular is that the method expects all sequences in the reference set to either be circular or linear. It cannot handle a mixture of both linear and circular reference genomes.

Beyond circular genomes, there are many other sequencing situations that would benefit from improved mapping methods. For example, many mappers have difficulty in identifying genome topologies, such as inversions. Most mapping methods also fail to identify haplotypes from short-read sequences. Further, there is increasing interest in mapping to multi-genome graphs (e.g., graphs composed of multiple human genomes for variation detection and/or diagnostic purposes, bacterial databases for species identification, or metagenomic assemblies for further assembly improvement and species separation) (e.g., as discussed in Vollmers et al., 2017, PLoS ONE 12(1):e0169662).

Given the growing need for genome sequencing and assembly of complex genomes, improved methods of graph-based, long-read mapping are needed in the art.

SUMMARY

The present disclosure addresses the shortcomings in graph-based mapping methods identified in the background by providing an improved method to determine the sequence of a nucleic acid based on long sequence reads. The method begins with obtaining a directed graph for a single diploid or polyploid organism of a species having a heterozygous genome, wherein the directed graph represents all or a portion of the heterozygous genome and comprises one or more nonlinear topological components. In some embodiments, each respective nonlinear topological component in the one or more nonlinear topological components represents a variation, with respect to a set of target sequences.

In some embodiments, each respective nonlinear topological component in the one or more nonlinear topological components has a corresponding initiating node and a corresponding terminal node that are connected by at least a corresponding first branch and a corresponding second branch, wherein one of the corresponding first branch and the corresponding second branch corresponds to the target sequence. In some embodiments, the directed graph is formed using a plurality of sequence reads from a biological sample of the single organism, which collectively have random error with respect to the target sequence that is greater than ten percent, by overlapping respective sequence reads in the plurality of sequence reads, wherein an amount of overhang between an overlapped first sequence read and second sequence is unrestricted provided there is a minimum consensus region between the first and second sequence reads.

The method proceeds by obtaining a query sequence from the biological sample in electronic format. The query sequence is either (i) a sequence read in the plurality of sequence reads, or (ii) a scaffold formed from the plurality of sequence reads. Moreover, the query sequence encompasses at least the corresponding initiating node or the corresponding terminal node of a first nonlinear topological component in the one or more nonlinear topological components.

The method continues by using the directed graph to form a mapping of the query sequence to the directed graph. The mapping of the query sequence comprises (i) a first alignment component to a first portion of the directed graph, (ii) a second alignment component to a second portion of the directed graph and (iii) a path describing a relation in the directed graph between the first portion and the second portion of the directed graph. In such instances, one of the first portion and the second portion is in the first or second branch of the first nonlinear topological component and the other of the first portion and the second portion is not in a branch of the first nonlinear topological component.

Other embodiments are directed to systems, portable consumer devices, and computer readable media associated with methods described herein.

Any embodiment disclosed herein can, when applicable, be applied to any other aspect.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications cited herein are incorporated by reference in their entireties. In the event of a conflict between a term herein and a term in an incorporated reference, the term herein controls.

BRIEF DESCRIPTION OF THE DRAWINGS

The implementations disclosed herein are illustrated by way of example, and not by way of limitation, in the figures of the accompanying drawings. Like reference numerals refer to corresponding parts throughout the several views of the drawings.

FIGS. 2A and 2B illustrate an example flowchart of a method of using a directed graph for mapping a query sequence, in which optional steps are depicted in dashed boxes, in accordance with some embodiments of the present disclosure.

FIGS. 8A and 8B collectively illustrate an example of transcriptome mapping via edges that define splice sites, in accordance with some embodiments of the present disclosure.

DETAILED DESCRIPTION

Figure 1:
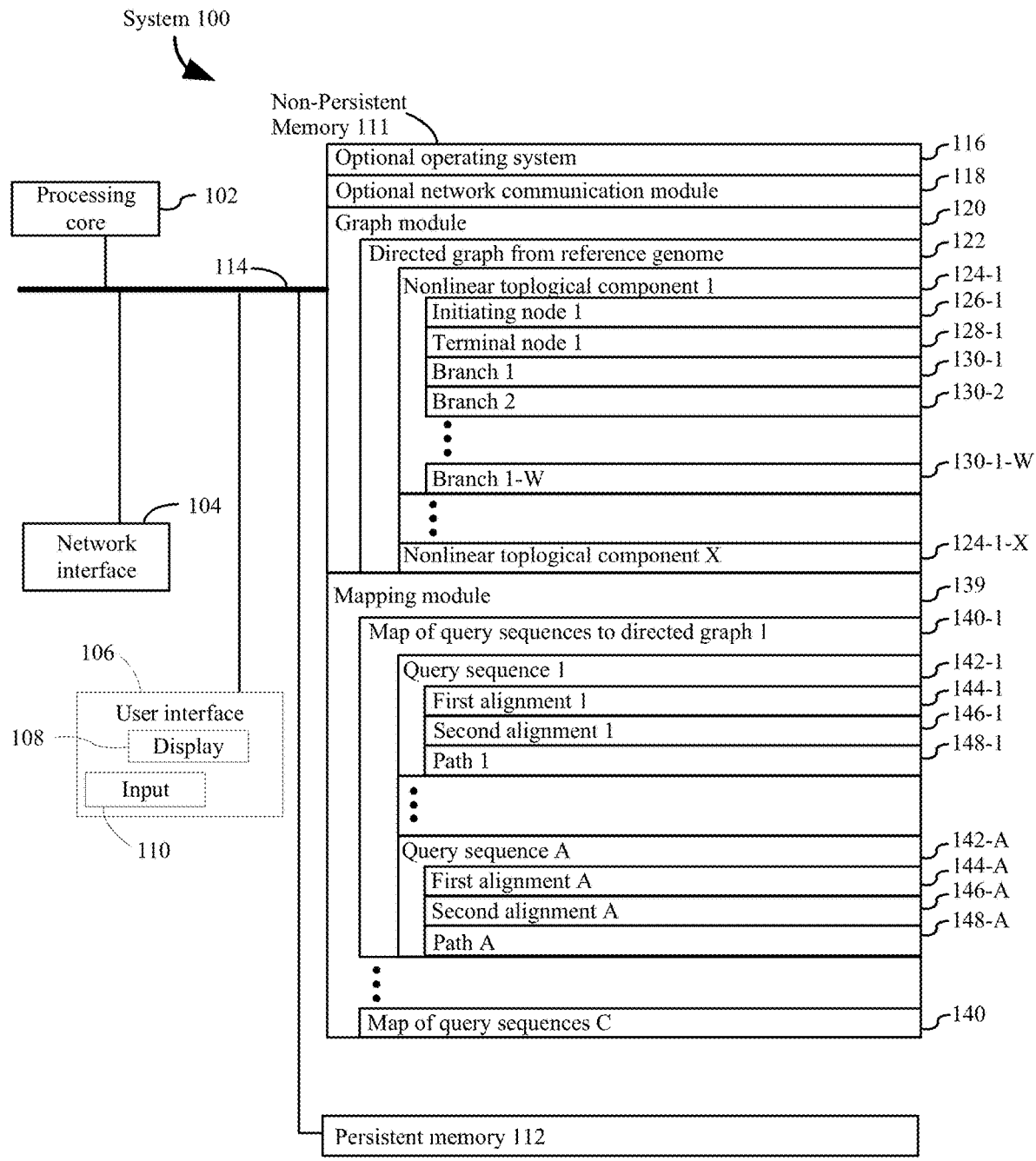
FIG. 1 illustrates an example block diagram illustrating a computing device, in accordance with some embodiments of the present disclosure.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

The implementations described herein provide various technical solutions for using long-read sequence reads. A directed graph, representing all or a portion of a genome, is obtained for a single diploid or polyploid organism that has a heterozygous genome. A query sequence (e.g., a sequence of interest) from a biological sample of the respective species of organism is also obtained. The directed graph is then used to form a mapping of the query sequence to the directed graph. Thus, the method enables detection of structural variants as well as single nucleotide variants. The methods provided herein require the use of long sequence reads.

Definitions

As used herein, the term "about" or "approximately" can mean within an acceptable error range for the particular value as determined by one of ordinary skill in the art, which can depend in part on how the value is measured or determined (e.g., the limitations of the measurement system). For example, "about" can mean within 1 or more than 1 standard deviation, per the practice in the art. "About" can mean a range of ±20%, ±10%, ±5%, or ±1% of a given value. The term "about" or "approximately" can mean within an order of magnitude, within 5-fold, or within 2-fold, of a value. Where particular values are described in the application and claims, unless otherwise stated the term "about" meaning within an acceptable error range for the particular value should be assumed. The term "about" can have the meaning as commonly understood by one of ordinary skill in the art. The term "about" can refer to ±10%. The term "about" can refer to ±5%.

As disclosed herein, the term "subject" refers to any living or non-living organism, including but not limited to a human (e.g., a male human, female human, fetus, pregnant female, child, or the like), a non-human animal, a plant, a bacterium, a fungus or a protist. Any human or non-human animal can be selected, including but not limited to mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale and shark. A subject may be a male or female of any stage (e.g., a man, a woman, or a child).

As used herein, the term "biological sample," "patient sample," or "sample" refers to any sample taken from a subject, which can reflect a biological state associated with the subject. Examples of biological samples include, but are not limited to, blood, whole blood, plasma, serum, urine, cerebrospinal fluid, fecal, saliva, sweat, tears, pleural fluid, pericardial fluid, or peritoneal fluid of the subject. A biological sample can include any tissue or material derived from a living or dead subject. A biological sample can be a cell-free sample. A biological sample can comprise a nucleic acid (e.g., DNA or RNA) or a fragment thereof. A sample can be a liquid sample or a solid sample (e.g., a cell or tissue sample). A biological sample can be a bodily fluid, such as blood, plasma, serum, urine, vaginal fluid, fluid from a hydrocele (e.g., of the testis), vaginal flushing fluids, pleural fluid, ascitic fluid, cerebrospinal fluid, saliva, sweat, tears, sputum, bronchoalveolar lavage fluid, discharge fluid from the nipple, aspiration fluid from different parts of the body (e.g., thyroid, breast), etc. A biological sample can be a stool sample. A biological sample can be treated to physically disrupt tissue or cell structure (e.g., centrifugation and/or cell lysis), thus releasing intracellular components into a solution which can further contain enzymes, buffers, salts, detergents, and the like which can be used to prepare the sample for analysis.

As used herein, the terms "nucleic acid" and "nucleic acid molecule" are used interchangeably. The terms refer to nucleic acids of any composition form, such as deoxyribonucleic acid (DNA, e.g., complementary DNA (cDNA), genomic DNA (gDNA) and the like), ribonucleic acid (RNA, e.g., message RNA (mRNA), short inhibitory RNA (siRNA), ribosomal RNA (rRNA), transfer RNA (tRNA), microRNA, RNA highly expressed by the fetus or placenta, and the like), and/or DNA or RNA analogs (e.g., containing base analogs, sugar analogs and/or a non-native backbone and the like), RNA/DNA hybrids and polyamide nucleic acids (PNAs), all of which can be in single- or double-stranded form. Unless otherwise limited, a nucleic acid can comprise known analogs of natural nucleotides, some of which can function in a similar manner as naturally occurring nucleotides. A nucleic acid can be in any form useful for conducting processes herein (e.g., linear, circular, supercoiled, single-stranded, double-stranded and the like). A nucleic acid may be, or may be from, a plasmid, phage, autonomously replicating sequence (ARS), centromere, artificial chromosome, chromosome, or other nucleic acid able to replicate or be replicated in vitro or in a host cell, a cell, a cell nucleus or cytoplasm of a cell in certain embodiments. A nucleic acid in some embodiments can be from a single chromosome or fragment thereof (e.g., a nucleic acid sample may be from one chromosome of a sample obtained from a diploid organism). In certain embodiments nucleic acids comprise nucleosomes, fragments or parts of nucleosomes or nucleosome-like structures. Nucleic acids sometimes comprise protein (e.g., histones, DNA binding proteins, and the like). Nucleic acids analyzed by processes described herein sometimes are substantially isolated and are not substantially associated with protein or other molecules. Nucleic acids also include derivatives, variants and analogs of RNA or DNA synthesized, replicated or amplified from single-stranded ("sense" or "antisense", "plus" strand or "minus" strand, "forward" reading frame or "reverse" reading frame) and double-stranded polynucleotides. Deoxyribonucleotides include deoxyadenosine, deoxycytidine, deoxyguanosine and deoxythymidine. For RNA, the base cytosine is replaced with uracil and the sugar 2' position includes a hydroxyl moiety. A nucleic acid may be prepared using a nucleic acid obtained from a subject as a template.

As used herein the term "ending position" or "end position" (or just "end") refers to the genomic coordinate or genomic identity or nucleotide identity of the outermost base, e.g., at the extremities, of a cell-free DNA molecule, e.g., plasma DNA molecule. The end position can correspond to either end of a DNA molecule. In this manner, if one refers to a start and end of a DNA molecule, both can correspond to an ending position. In some cases, one end position is the genomic coordinate or the nucleotide identity of the outermost base on one extremity of a cell-free DNA molecule that is detected or determined by an analytical method, e.g., massively parallel sequencing or next-generation sequencing, single molecule sequencing, double- or single-stranded DNA sequencing library preparation protocols, polymerase chain reaction (PCR), or microarray. In some cases, such in vitro techniques can alter the true in vivo physical end(s) of the cell-free DNA molecules. Thus, each detectable end can represent the biologically true end or the end is one or more nucleotides inwards or one or more nucleotides extended from the original end of the molecule e.g., 5' blunting and 3' filling of overhangs of non-blunt-ended double stranded DNA molecules by the Klenow fragment. The genomic identity or genomic coordinate of the end position can be derived from results of alignment of sequence reads to a human reference genome, e.g., hg19. It can be derived from a catalog of indices or codes that represent the original coordinates of the human genome. It can refer to a position or nucleotide identity on a cell-free DNA molecule that is read by but not limited to target-specific probes, mini-sequencing, DNA amplification. The term "genomic position" can refer to a nucleotide position in a polynucleotide (e.g., a gene, a plasmid, a nucleic acid fragment, a viral DNA fragment). The term "genomic position" is not limited to nucleotide positions within a genome (e.g., the haploid set of chromosomes in a gamete or microorganism, or in each cell of a multicellular organism).

As used herein, the term "fragment" (e.g., a DNA fragment), refers to a portion of a polynucleotide or polypeptide sequence that comprises at least three consecutive nucleotides. A nucleic acid fragment can retain the biological activity and/or some characteristics of the parent polynucleotide. In an example, nasopharyngeal cancer cells can deposit fragments of Epstein-Barr Virus (EBV) DNA into the bloodstream of a subject, e.g., a patient. These fragments can comprise one or more BamHI-W sequence fragments, which can be used to detect the level of tumor-derived DNA in the plasma. The BamHI-W sequence fragment corresponds to a sequence that can be recognized and/or digested using the Bam-HI restriction enzyme. The BamHI-W sequence can refer to the sequence 5'-GGATCC-3'.

As used herein, a "local maximum" can refer to a genomic position (e.g., a nucleotide) at which the largest value of the parameter of interest is obtained when compared with the neighboring positions or refer to the value of the parameter of interest at such a genomic position. As examples, the neighboring positions can range from 50 bp to 2000 bp. Examples for the parameter of interest include, but are not limited to, the number of fragments ending on a genomic position, the number of fragments overlapping with the position, or the proportion of fragments covering the genomic position that are larger than a threshold size. Many local maxima can occur when the parameter of interest has a periodic structure. A global maximum is a specific one of the local maxima. Similarly, a "local minimum" refers to a genomic position at which the smallest value of the parameter of interest is obtained when compared with the neighboring positions or refer to the value of the parameter of interest at such a genomic position.

As used herein, the term "rate" of nucleic acid molecules (e.g., DNA or RNA) ending on a position can relate to how frequently a nucleic acid molecule ends on the position. The rate can be based on a number of nucleic acid molecules that end on the position normalized against a number of nucleic acid molecules analyzed. The rate can be based on a number of nucleic acid molecules that end on the position normalized against a number of nucleic acid molecules that end on a different position. The rate can be based on a number of nucleic acid molecules from a first sample that end on the position normalized against a number of nucleic acid molecules from a second sample (e.g., a reference sample) that end on the position. The rate can be based on a number of nucleic acid molecules from a first sample that end on a first set of positions (e.g., genomic positions) normalized against a number of nucleic acid molecules from a second sample (e.g., a reference sample) that end on a second set of positions. Accordingly, the rate can correspond to a frequency of how many nucleic acid molecules end on a position, and in some cases does not relate to a periodicity of positions having a local maximum in the number of nucleic acid molecules ending on the position.

As used herein, the term "relative abundance" can refer to a ratio of a first amount of nucleic acid fragments having a particular characteristic (e.g., a specified length, ending at one or more specified coordinates/ending positions, or aligning to a particular region of the genome) to a second amount nucleic acid fragments having a particular characteristic (e.g., a specified length, ending at one or more specified coordinates/ending positions, or aligning to a particular region of the genome). In one example, relative abundance may refer to a ratio of the number of DNA fragments ending at a first set of genomic positions to the number of DNA fragments ending at a second set of genomic positions. In some aspects, a "relative abundance" can be a type of separation value that relates an amount (one value) of DNA molecules ending within one window of genomic position to an amount (other value) of DNA molecules ending within another window of genomic positions. The two windows can overlap, but can be of different sizes. In other implementations, the two windows cannot overlap. Further, the windows can be of a width of one nucleotide, and therefore be equivalent to one genomic position.

As used herein, the term "reference genome" refers to any particular known, sequenced or characterized genome, whether partial or complete, of any organism or virus that may be used to reference identified sequences from a subject. Exemplary reference genomes used for human subjects as well as many other organisms are provided in the on-line genome browser hosted by the National Center for Biotechnology Information ("NCBI") or the University of California, Santa Cruz (UCSC). A "genome" refers to the complete genetic information of an organism or virus, expressed in nucleic acid sequences. As used herein, a reference sequence or reference genome often is an assembled or partially assembled genomic sequence from an individual or multiple individuals. In some embodiments, a reference genome is an assembled or partially assembled genomic sequence from one or more human individuals. The reference genome can be viewed as a representative example of a species' set of genes. In some embodiments, a reference genome comprises sequences assigned to chromosomes. Exemplary human reference genomes include but are not limited to NCBI build 34 (UCSC equivalent: hg16), NCBI build 35 (UCSC equivalent: hg17), NCBI build 36.1 (UCSC equivalent: hg18), GRCh37 (UCSC equivalent: hg19), and GRCh38 (UCSC equivalent: hg38).

As used herein, the term "sequence reads" or "reads" refers to nucleotide sequences produced by any sequencing process described herein or known in the art. Reads can be generated from one end of nucleic acid fragments ("single-end reads"), and sometimes are generated from both ends of nucleic acid fragments (e.g., paired-end reads, double-end reads, or mate-pair reads). The length of the sequence read is often associated with the particular sequencing technology. In some embodiments, the sequence reads are of a mean, median or average length of about 5,000 bp to 50,000 bp long (e.g., about 5,000 bp, about 7,500 bp, about 10,000 bp, about 12,500 bp, about 15,000 bp, about 20,000 bp, about 25,000 bp, about 30,000 bp, about 35,000 bp, about 40,000 bp, about 45,000 bp, about 50,000 bp, about 55,000, about 60,000, about 65,000, about 70,000, about 75,000, or about 80,000). In some embodiments, the sequence reads are of a mean, median or average length of about 1000 bp, 2000 bp, 5000 bp, 10,000 bp, 50,000 bp or more. A sequence read (or sequencing read) can refer to sequence information corresponding to a nucleic acid molecule (e.g., a string of nucleotides). For example, a sequence read can correspond to a string of nucleotides (e.g., of up to about 50,000 bp) from part of a nucleic acid fragment, can correspond to a string of nucleotides at one or both ends of a nucleic acid fragment, or can correspond to nucleotides of the entire nucleic acid fragment. A sequence read can be obtained in a variety of ways, e.g., using sequencing techniques or using probes, e.g., in hybridization arrays or capture probes, or amplification techniques, such as the polymerase chain reaction (PCR) or linear amplification using a single primer or isothermal amplification.

As used herein, the terms "sequencing," "sequence determination," and the like as used herein refers generally to any and all biochemical processes that may be used to determine the order of biological macromolecules such as nucleic acids or proteins. For example, sequencing data can include all or a portion of the nucleotide bases in a nucleic acid molecule such as a DNA fragment.

As used herein, the terms "single nucleotide variant," "single nucleotide polymorphism," or "SNP" refer to a substitution of one nucleotide to a different nucleotide at a position (e.g., site) of a nucleotide sequence, e.g., a sequence read from an individual. A substitution from a first nucleobase X to a second nucleobase Y may be denoted as "X>Y." For example, a cytosine to thymine SNP may be denoted as "C>T." The term "het-SNP" refers to a heterozygous SNP, where the genome is at least diploid and at least one—but not all—of the two or more homologous sequences exhibits the particular SNP. Similarly, a "hom-SNP" is a homologous SNP, where each homologous sequence of a polyploid genome has the same variant compared to the reference genome. As used herein, the term "structural variant" or "SV" refers to large (e.g., larger than 1 kb) regions of a genome that have undergone physical transformations such as inversions, insertions, deletions, or duplications (e.g., see review of human genome SVs by Spielmann et al., 2018, Nat Rev Genetics 19:453-467).

As used herein, the terms "collapsed reads," "collapsed sequence reads," or "collapsed region" refer to a plurality of sequence reads that originate from a similar region of a polynucleotide molecule and have been combined into one resulting sequence. For example, as part of sequence determination, a plurality of reads from a polynucleotide may be compared to each other (e.g., to provide a consensus sequence of the original polynucleotide). Further, the resulting collapsed read may include information regarding nucleotide mismatches, insertions, or deletions. Using collapsed reads in nucleotide sequencing provides a higher degree of certainty of the sequencing result (e.g., instead of relying on a single sequence read for each region of the polynucleotide that is being sequenced).

As used herein, the term "node" refers to a sequence read and the term "branch" refers to the overlap between two separate sequence reads (e.g., nodes). A directed graph comprises multiple nodes and multiple branches. Collapsed reads are aligned to a directed graph such that any of the collapsed reads may be represented in order by a subset of the edges and corresponding vertices (e.g., nodes). As described by Compeau et al., branches (e.g., directed edges) can indicate directionality of the overlap between nodes, thus helping to determine the overall topological organization of multiple nodes (Nat Biotechnol 29(11):987-991, 2011). This is the basis of forming directed graphs. De Bruijn graphs are typically derived from sequence reads that have a predefined overlap, a method which is ideal for short-read sequencing. This may be achieved either by splitting reads into specified lengths (e.g., k-mers) or by defining the length of edges (Id.). Typically, the overlap will be k−1 for cases where the reads are chopped into k-mers. A used herein, the term "k-mer" refers to a set length of DNA sequence. Unidirectional edges of the directed graph represent sequences of k nucleotide bases (e.g., "k-mers") in the target region, and the edges are connected by vertices (or nodes).

As used herein, the term "nonlinear topological component" or "nonlinear component" refers to a complex nucleic acid sequence. In particular, such components may be sequence reads containing one or more variants, where the different options for the mapped sequence at one or more locations are indicated. Alternately, a nonlinear component may comprise a circular nucleic acid. In some instances, these variants can be structural variations (SVs), single nucleotide variations (SNPs), small nucleotide variation, or a region with an elevated number of het-SNPs that is modeled as a larger replacement event.

As used herein, the term "haplotig" refers to a haplotype contig. A contig comprises a contiguous set of overlapping nucleic acid segments, representing a consensus region of nucleic acid (e.g., of a genome). And a haplotype includes several polymorphisms that are typically inherited together (e.g., those which are located near each other within a set region of a genome, for example a chromosome). Formally, a haplotig is "a contig of clones with the same haplotype," as described in Makoff and Flomen, 2007, Genome Bio 8(6):R114.

As used herein, the term "phasing" refers to identifying alleles in a diploid or polyploid genome. In particular, phasing is used to determine which alleles belong together on individual chromosomes or in specified regions of a genome. Methods of phasing human genomes are described in Choi et al., 2018, PLOS Genetics 14(4):e1007308, which is hereby incorporated in its entirety by reference.

The terminology used herein is for the purpose of describing particular cases only and is not intended to be limiting. As used herein, the singular forms "a," "an" and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

Several aspects are described below with reference to example applications for illustration. It should be understood that numerous specific details, relationships, and methods are set forth to provide a full understanding of the features described herein. One having ordinary skill in the relevant art, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

Exemplary System Embodiments

Details of an exemplary system are now described in conjunction with FIG. 1. FIG. 1 is a block diagram illustrating system 100 in accordance with some implementations. The device 100 in some implementations includes one or more processing units (CPU(s)) 102—also referred to as processors or processing core, one or more network interfaces 104, a user interface 106, a non-persistent memory 111, a persistent memory 112, and one or more communication buses 114 for interconnecting these components. One or more communication buses 114 optionally include circuitry (sometimes called a chipset) that interconnects and controls communications between system components. Non-persistent memory 111 typically includes high-speed random access memory, such as DRAM, SRAM, DDR RAM, ROM, EEPROM, flash memory, whereas the persistent memory 112 typically includes CD-ROM, digital versatile disks (DVD) or other optical storage, magnetic cassettes, magnetic tape, magnetic disk storage or other magnetic storage devices, magnetic disk storage devices, optical disk storage devices, flash memory devices, or other non-volatile solid state storage devices. The persistent memory 112 optionally includes one or more storage devices remotely located from the CPU(s) 102. Persistent memory 112, and the non-volatile memory device(s) within non-persistent memory 112, comprise non-transitory computer readable storage medium. In some implementations, non-persistent memory 111 or alternatively the non-transitory computer readable storage medium stores the following programs, modules and data structures, or a subset thereof, sometimes in conjunction with the persistent memory 112:

- an optional operating system 116, which includes procedures for handling various basic system services and for performing hardware dependent tasks;
- an optional network communication module (or instructions) 118 for connecting the system 100 with other devices, or a communication network;
- a graph module 120 for mapping long sequence reads to a directed graph that includes a directed graph 122 of an organism with a heterozygous genome that comprises at least one nonlinear topological component 124, each nonlinear topological component comprising an initiating node 126 and a terminal node 128, and each pair of nodes being connected by at least a corresponding first branch 130-1 and a corresponding second branch 130-2; and
- a mapping module 139 that comprises a map of query sequence(s) 140 to directed graph 122, each map comprising one or more query sequences 142, each of which query sequences comprises at least a first alignment 144, a second alignment 146, and a path 148 of the topological relationship between the first and second alignments.

In some embodiments, directed graph 122 is derived from a de novo assembly of sequence reads or contigs. In some embodiments, directed graph 122 is derived from a reference genome (e.g., one or more existing annotations). In some embodiments, the sequence reads used to form the directed graph are derived from a biological sample of the organism, and the sequence reads collectively have random error with respect to the set of target sequences.

In some embodiments, a query sequence 142 comprises either a sequence read in the plurality of sequence reads, or a scaffold (e.g., a contig, unitig, or haplotig) formed from the plurality of sequence reads. In some embodiments, query sequence 142 describes at least the initiating or the terminal node of a respective nonlinear topological component 124.

In various implementations, one or more of the above identified elements are stored in one or more of the previously mentioned memory devices, and correspond to a set of instructions for performing a function described above. The above identified modules, data, or programs (e.g., sets of instructions) need not be implemented as separate software programs, procedures, datasets, or modules, and thus various subsets of these modules and data may be combined or otherwise re-arranged in various implementations. In some implementations, non-persistent memory 111 optionally stores a subset of the modules and data structures identified above. Furthermore, in some embodiments, the memory stores additional modules and data structures not described above. In some embodiments, one or more of the above identified elements is stored in a computer system, other than that of visualization system 100, that is addressable by visualization system 100 so that visualization system 100 may retrieve all or a portion of such data when needed.

Although FIG. 1 depicts a "system 100," the figure is intended more as functional description of the various features which may be present in computer systems than as a structural schematic of the implementations described herein. In practice, and as recognized by those of ordinary skill in the art, items shown separately could be combined and some items could be separated. Moreover, although FIG. 1 depicts certain data and modules in non-persistent memory 111, some or all of these data and modules may be in persistent memory 112.

Figure 2B:
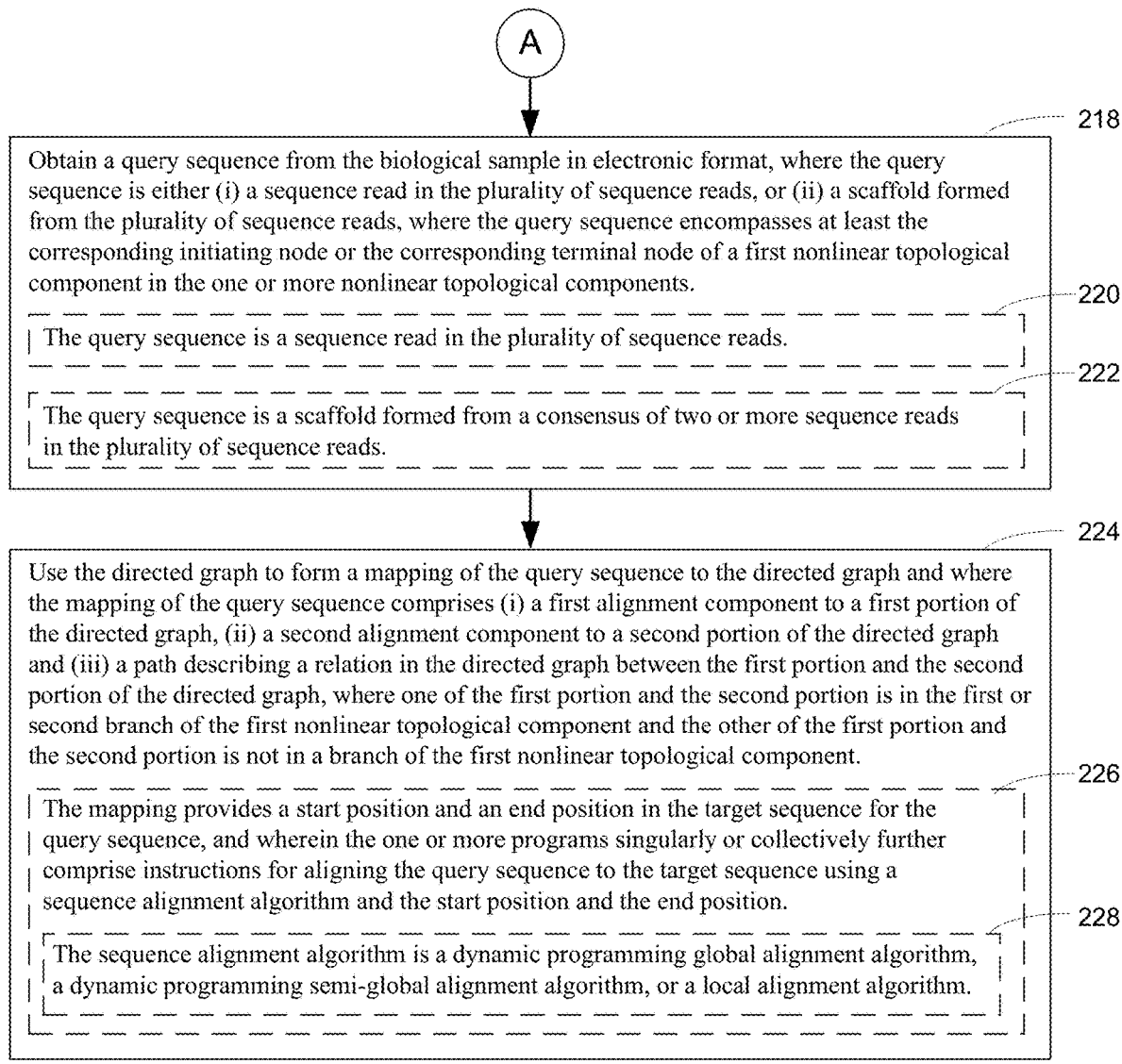

While a system in accordance with the present disclosure has been disclosed with reference to FIG. 1, methods in accordance with the present disclosure are now detailed with reference to FIGS. 2A and 2B.

Using a Graph while Mapping Long Sequence Reads or Contigs to a Target Sequence

Block 202.

A method of sequencing nucleic acids via graph based mapping, is provided.

In some embodiments, a target sequence would be a sequence to which queries are mapped. A target sequence can include any type of sequence such as a reference genome, or assembled contigs, unitigs, or scaffolding.

Block 204.

Using the computer system 100, there is obtained a directed graph for a single diploid or polyploid organism of a species having a heterozygous genome, where the directed graph represents all or a portion of the heterozygous genome and comprises one or more nonlinear topological components (e.g., bubbles or cycles). In some embodiments, each respective nonlinear topological component in the one or more nonlinear topological components represents a variation (e.g., a structural variation, single nucleotide variation (SNP), small nucleotide variation, or region that is heavy in het-SNPs and modeled as a larger replacement event) with respect to a set of target sequences.

In some embodiments, the directed graph represents at least ten percent of the heterozygous genome, and the directed graph comprises ten or more nonlinear topological components.

In some embodiments, the directed graph represents at least fifty percent of the heterozygous genome, and the directed graph comprises twenty-five or more nonlinear topological components.

In some embodiments, the directed graph represents at least five percent of the heterozygous genome, at least ten percent of the heterozygous genome, at least twenty percent of the heterozygous genome, at least thirty percent of the heterozygous genome, at least forty percent of the heterozygous genome, at least fifty percent of the heterozygous genome, at least seventy-five percent of the heterozygous genome, at least ninety percent of the heterozygous genome, or at least one hundred percent of the heterozygous genome.

In some embodiments, the directed graph includes a plurality of nodes, e.g., each of which may represent a sequence read. Accordingly, the total number of nodes in a directed graph will be proportional to the size of the genome, or portion of the genome being mapped. For instance, in some embodiments where a large proportion of a complex diploid and higher order polyploid genome is being mapped, the directed graph will have at least 10,000 nodes. In some embodiments, the directed graph will have at least 100,000 nodes. In some embodiments, the directed graph will have at least 500,000 nodes. In other embodiments, the directed graph will have at least 1 million, two million, three million, four million, five million, or more nodes.

In some embodiments, the directed graph comprises two or more nonlinear topological components, five or more nonlinear topological components, ten or more nonlinear topological components, twenty-five or more nonlinear topological components, fifty or more nonlinear topological components, or one hundred or more nonlinear topological components.

In some embodiments, for instance where a large proportion of a complex diploid or higher order polyploid genome is being mapped, the directed graph will have at least 1,000 nonlinear topological components. In some embodiments, the directed graph will have at least 10,000 nonlinear topological components. In some embodiments, the directed graph will have at least 100,000 nonlinear topological components. In other embodiments, the directed graph will have at least 500,000, 1 million, two million, three million, four million, five million, or more nonlinear topological components. In some embodiments, there is a non-linear element in the graph for each heterozygous allele in the subject having at least one sequence read mapped to each of the possible alleles. That is, where every SNP and every INDEL observed in which at least one sequence read has mapped to allele 1 and at least one read has mapped to allele 2.

In some embodiments, the directed graph comprises any combination of the above percentages of the heterozygous genome, the number of nodes, and the number of nonlinear topological components.

In some embodiments, each respective nonlinear topological component in the one or more nonlinear topological components has a corresponding initiating node and a corresponding terminal node that are connected by at least a corresponding first branch and a corresponding second branch. In such embodiments, the corresponding first branch and the corresponding second branch corresponds to (e.g., maps to) the target sequence. In some embodiments, the set of target sequences represents one or more of: (i) a reference sequence of the species or (ii) assembled contigs, unitigs, haplotigs or scaffolds. The assembly can be performed either de novo or by mapping a plurality of sequencing reads to another target sequence.

In some embodiments, the corresponding first and second branch of a nonlinear topological component in the one or more nonlinear topological components respectively represent a first allele and a second allele for a variation in the heterozygous genome. In some embodiments, there may be more branches and/or more alleles. For example, in some embodiments the genome of the organism is polyploid and not merely diploid, and there may exist as many alleles as there are chromosome pairs. In some embodiments, the one or more nonlinear topological components comprise three corresponding branches and three respective alleles, four corresponding branches and four respective alleles, five corresponding branches and five respective alleles, or six corresponding branches and six respective alleles.

The directed graph is formed using a plurality of sequence reads from a biological sample of the single organism, which collectively have random error with respect to the target sequence that is greater than ten percent, by overlapping respective sequence reads in the plurality of sequence reads, wherein an amount of overhang between an overlapped first sequence read and second sequence is unrestricted provided there is a minimum consensus region between the first and second sequence reads (e.g., thus distinguishing the method described herein over de Bruijn graphs). In some embodiments, the plurality of sequence reads has an average sequence length of greater than 10,000 base pairs.

In some embodiments, the plurality of sequence reads has an average length of greater than 2,500 base pairs, greater than 5,000 base pairs, greater than 10,000 base pairs, greater than 15,000 base pairs, greater than 20,000 base pairs, greater than 50,000 base pairs, or greater than 100,000 base pairs.

Block 218.

Using computer system 100, there is obtained a query sequence from the biological sample in electronic format. The query sequence is either (i) a sequence read in the plurality of sequence reads or (ii) a scaffold (e.g., contig, unitig, or haplotig) formed from the plurality of sequence reads. Here, the query sequence encompasses at least the corresponding initiating node or the corresponding terminal node of a first nonlinear topological component in the one or more nonlinear topological components.

In some embodiments, the query sequence is a sequence read in the plurality of sequence reads. In some embodiments, the query sequence is a scaffold formed from a consensus of two or more sequence reads in the plurality of sequence reads.

In some embodiments, the query sequence is obtained via single-molecule, real-time (SMRT) sequencing, which generally provides long sequence reads. In some embodiments, the SMRT sequencing is performed as described by Rhoads and Au (Genomics Proteomics Bioinformatics 13:278-289, 2015). Such long read sequencing provide sufficient information to be used alone for de novo whole genome sequencing (e.g., as described in Chin et al., 2013, Nat Methods 10(6):563-569).

Block 224.

The method proceeds by using the directed graph to form a mapping of the query sequence to the directed graph. The mapping of the query sequence comprises (i) a first alignment component to a first portion of the directed graph, (ii) a second alignment component to a second portion of the directed graph and (iii) a path describing a relation in the directed graph between the first portion and the second portion of the directed graph. In such instances, one of the first portion and the second portion is in the first or second branch of the first nonlinear topological component and the other of the first portion and the second portion is not in a branch of the first nonlinear topological component. In some embodiments, there is more than two branches per nonlinear topological component, and the same query can also span multiple nonlinear topological component (e.g., large contig mapped to a reference graph).

In some embodiments, a nonlinear topological component comprises at least 2 branches, at least 3 branches, at least 4 branches, at least 5 branches, at least 6 branches, at least 7 branches, at least 8 branches, at least 9 branches, or at least 10 branches.

In some embodiments, the mapping provides a start position and an end position in the target sequence for the query sequence. In some embodiments, the one or more programs singularly or collectively further comprise instructions for aligning the query sequence to the target sequence using a sequence alignment algorithm and the start position and the end position.

In some embodiments, the sequence alignment algorithm is a dynamic programming global alignment algorithm, a dynamic programming semi-global alignment algorithm, or a dynamic programming local alignment algorithm.

Different alignment algorithms have different efficiencies or are tuned for better detection of particular genomic features. Indeed, there is a wide range of different types of algorithms as discussed below. GASSST (global alignment short sequence search tool) is designed for improved detection of indels (e.g., as described by Rizk and Lavenier, Bioinformatics 26(20):2534-2540, 2010). The Burrows-Wheeler Aligner's Smith-Waterman Alignment (BWA-SW) method is designed for improved efficiency using long-read sequences (e.g., as described by Li and Durbin, Bioinformatics 26(5):589-595, 2010). Parasail was developed to provide faster intra-sequence local pairwise alignments (e.g., as described by Daily, BMC Bioinformatics 17:81, 2016). Skewer is specifically focused on using next-generation sequencing paired-end reads (e.g., as described in Jiang et al., 2014, BMC Bioinformatics 15:182). DNACLUST is intended to improve clustering efficiency for sequences of highly similar DNA regions (e.g., as described by Ghodsi et al., 2011, BMC Bioinformatics 12:271). There is a longer history of local alignment algorithms, which include such ubiquitous methods as BLAST and Smith-Waterman (Altschul et al., 1990, J Mol Biol 215:403-410; Smith and Waterman, 1981, J Mol Biol 147(1):195-197). However, there are also more recently developed methods that seek to improve on the initial algorithms. For example, Bowtie 2 has improved performance for gapped alignment (e.g., as described by Langmead and Salzberg, Nat Methods 9(4): 357-359, 2012). Li and Homer provide a comparison of different sequence alignment algorithms, in particular concluding that long-read sequencing enables obtaining more detailed genome information than is available from sequencing based on short reads (Briefings in Bioinformatics 11(5): 473-483, 2010).

Forming a Directed Graph while Mapping Long Sequence Reads or Contigs to a Target Sequence.

In some embodiments of the present disclosure, a nucleic acid sequencing method is provided for constructing a directed graph for a single diploid or polyploid organism of a species having a heterozygous genome. This method proceeds by mapping a plurality of sequence reads obtained from a biological sample of the organism onto a target sequence of the species. The plurality of sequence reads collectively have a random error with respect to the target sequence that is greater than ten percent. The directed graph represents all or a portion of the heterozygous genome and comprises one or more nonlinear topological components (e.g., bubbles or cycles). Each respective nonlinear topological component in the one or more nonlinear topological components represents a variation (where a variation is, for example, one of the set of structural variation, single nucleotide variation (SNP), small nucleotide variation, or a region that is heavy in het-SNPs and modeled as a larger replacement event) with respect to the reference sequence. Each respective nonlinear topological component in the one or more nonlinear topological components has a corresponding initiating node and a corresponding terminal node that are connected by at least a corresponding first branch and a corresponding second branch. One of the corresponding first branch and the corresponding second branch corresponds to the target sequence and the other of the corresponding first branch and the corresponding second branch corresponds to a variation, identified by the mapping, in one or more sequence reads in the plurality of sequence reads.

In some embodiments, the mapping provides a start position and an end position in the target sequence for a sequence read in the plurality of sequence reads. In such embodiments the sequence read is aligned to the target sequence using a sequence alignment algorithm and the start position and the end position for the sequence read.

In some embodiments, the directed graph represents at least ten percent of the genome of the species, at least twenty percent of the genome of the species, at least thirty percent of the genome of the species, at least forty percent of the genome of the species, at least fifty percent of the genome of the species, at least sixty percent of the genome of the species, or at least seventy percent of the genome of the species.

In some embodiments, the directed graph includes a plurality of nodes, e.g., each of which may represent a sequence read. Accordingly, the total number of nodes in a directed graph will be proportional to the size of the genome, or portion of the genome being mapped. For instance, in some embodiments where a large proportion of a complex diploid and higher order polyploid genome is being mapped, the directed graph will have at least 10,000 nodes. In some embodiments, the directed graph will have at least 100,000 nodes. In some embodiments, the directed graph will have at least 500,000 nodes. In other embodiments, the directed graph will have at least 1 million, two million, three million, four million, five million, or more nodes.

In some embodiments, for instance where a large proportion of a complex diploid or higher order polyploid genome is being mapped, the directed graph will have at least 1,000 nonlinear topological components. In some embodiments, the directed graph will have at least 10,000 nonlinear topological components. In some embodiments, the directed graph will have at least 100,000 nonlinear topological components. In other embodiments, the directed graph will have at least 500,000, 1 million, two million, three million, four million, five million, or more nonlinear topological components. In some embodiments, there is a non-linear element in the graph for each heterozygous allele in the subject having at least one sequence read mapped to each of the possible alleles. That is, where every SNP and every INDEL observed in which at least one sequence read has mapped to allele 1 and at least one read has mapped to allele 2.

Use Case 1: Forming a Graph from Phased De Novo Assembly of Long Sequencing Reads.

Typical mapping methods are generally ill-equipped to handle haplotigs. Using a normal mapper and only a primary assembly as the reference, a haplotig would be broken in the regions of the structural variations—graph bubbles—into a primary and one or more supplementary alignments. For example, some mappers (e.g., such as BLASR with the "--bestn 1" option selected) would report only the primary alignment (see Chaisson and Tesler BMC Bioinformatics 13:238, 2012). However, this obscures some of the underlying genetic variation.

A nucleic acid sequencing method is provided that comprises constructing a haplotig assembly graph for a single diploid or polyploid organism of a species having a heterozygous genome. In some embodiments, the haplotig assembly graph represents the heterozygous genome and comprises one or more nonlinear topological components (e.g., bubbles or cycles). Each respective nonlinear topological component in the one or more nonlinear topological components has a corresponding initiating node and a corresponding terminal node that are connected by at least a corresponding first branch and a corresponding second branch. The corresponding first and second branch respectively represent a first and second phased haplotig corresponding to a first and second homologous chromosome in the heterozygous genome.

In some embodiments, there may be more branches and/or more alleles. For example, in some embodiments the genome of the organism is polyploid and not merely diploid, and there may exist as many alleles as there are chromosome pairs. In some embodiments, the one or more nonlinear topological components comprise three corresponding branches and three respective alleles, four corresponding branches and four respective alleles, five corresponding branches and five respective alleles, or six corresponding branches and six respective alleles The sequencing method continues by obtaining a haplotig derived from a plurality of sequence reads from a biological sample obtained from the single diploid or polyploid organism in electronic format. The haplotig encompasses at least the corresponding initiating node or the corresponding terminal node of a first nonlinear topological component in the one or more nonlinear topological components. The method proceeds with using the haplotig assembly graph to form a mapping of the haplotig. The mapping of the haplotig comprises (i) a first alignment component to a first portion of the haplotig assembly graph, (ii) a second alignment component to a second portion of the haplotig assembly graph and (iii) a path describing a relation in the haplotig assembly graph between the first portion and the second portion of the haplotig assembly graph. One of the first portion and the second portion is in the first or second branch of the first nonlinear topological component and the other of the first portion and the second portion is not in a branch of the first nonlinear topological component.

In some embodiments, the mapping provides a start position and an end position in a target sequence for the haplotig. The one or more programs, singularly or collectively, further comprise instructions for aligning the haplotig to a target sequence for the species using a sequence alignment algorithm and the start position and the end position.

In some embodiments, the haplotig assembly graph represents at least ten percent of the heterozygous genome, and the haplotig assembly graph comprises ten or more nonlinear topological components. In some embodiments, the haplotig assembly graph represents at least fifty percent of the heterozygous genome, and the haplotig assembly graph comprises twenty-five or more nonlinear topological components.

In some embodiments the haplotig assembly graph represents at least five percent of the heterozygous genome, at least ten percent of the heterozygous genome, at least twenty percent of the heterozygous genome, at least thirty percent of the heterozygous genome, at least forty percent of the heterozygous genome, at least fifty percent of the heterozygous genome, at least seventy-five percent of the heterozygous genome, at least ninety percent of the heterozygous genome, or at least one hundred percent of the heterozygous genome.

In some embodiments, the haplotig assembly graph comprises two or more nonlinear topological components, five or more nonlinear topological components, ten or more nonlinear topological components, twenty-five or more nonlinear topological components, fifty or more nonlinear topological components, or one hundred or more nonlinear topological components.

In some embodiments, the haplotig assembly graph comprises any combination of the above percentages of the heterozygous genome and the number of nonlinear topological components.

In some embodiments, the haplotig assembly graph is formed using the plurality of sequence reads by overlapping respective sequence reads in the plurality of sequence reads, wherein an amount of overhang between an overlapped first sequence read and second sequence is unrestricted provided there is a minimum consensus region between the first and second sequence reads (e.g., to distinguish over de Bruijn graphs, which have a predefined overlap length).

In some embodiments, the minimum consensus region comprises at least 1 base, at least 2 bases, at least 3 bases, at least 4 bases, at least 5 bases, at least 6 bases, at least 7 bases, at least 8 bases, at least at least 9 bases, at least 10 bases, at least 15 bases, at least 20 bases, at least 30 bases, at least 40 bases, at least 50 bases, at least 60 bases, at least 70 bases, at least 80 bases, at least 90 bases, at least 100 bases, at least 500 bases, or at least 1000 bases. In some embodiments, each consensus region has the same overlap length. In some embodiments, each consensus region has a different overlap length. In some embodiments, a first set of consensus regions have a first overlap length and a second set of consensus regions have a second overlap length.

Figure 3:
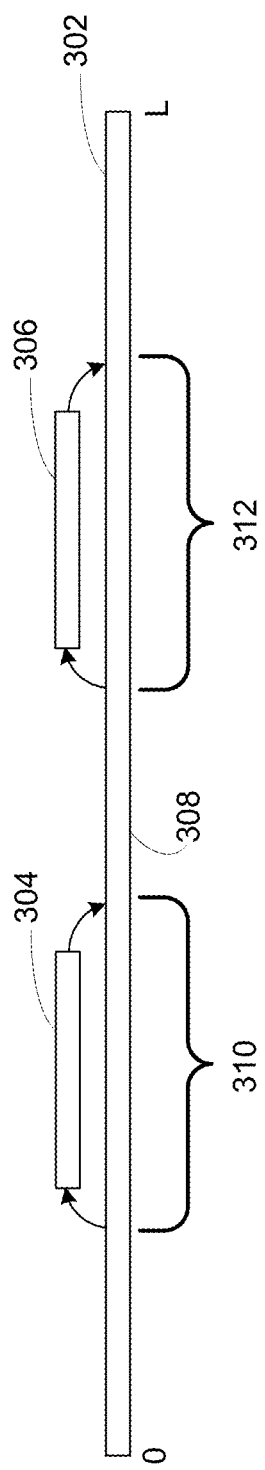
FIG. 3 illustrates an example of aligning phased haplotigs across assembled genomes, in accordance with some embodiments of the present disclosure.

FIG. 3 illustrates an example of the output from aligning phased haplotigs across assembled genomes containing structural variation between haplotypes. Haplotig phasing is applicable to FALCON-unzip assembly methods, which is intended as a diploid assembler (e.g., as described in Chin et al., 2016, Nat Methods 13(12):1050-1054). In some embodiments, the disclosed method is applied herein to enhance FALCON-unzip assembly by enabling accurate haplotig placement and construction of a less fragmented haplotig graph (and also longer phased haplotigs). In some embodiments, the resulting assembly is output in a graph format to retain as much information as possible regarding divergent haplotypes (e.g., as opposed to a FASTA output format that merely provides a linear contig).

In FIG. 3, a primary contig 302 is shown with two associated contigs 304 and 306, producing respective bubbles 310 and 312. In some embodiments, sequence reads that map optimally within a single contig produce a continuous alignment. In some embodiments, the reads that map across one or more branching locations are reported as split alignments with an accompanying alignment path. In some embodiments, a score is assigned to each alignment. In some embodiments, each score indicates the quality of a respective alignment. In some embodiments, only alignments with a score above a threshold value are reported. In some embodiments, if there is more than one alignment with an associated score above the threshold value, then every such alignment is reported.

In some embodiments, the quality score is reported in the SAM format (e.g., as described in 'Sequence Alignment/Map Format Specification' on the Internet at samtools.github.io/hts-specs/SAMv1.pdf.

In some embodiments, the threshold value for scores is at least 1, at least 5, at least 10, at least 15, at least 20, at least 25, at least 30, at least 35, at least 40, at least 45, at least 50, or at least 55.

In some embodiments, a quality score is calculated using a sum of each base quality score for all alignments in a given sequence read, and a sum of the quality scores for each mismatched base (e.g., as described by Li et al., 2008, Genome Res 18(11):1851-1858, which is hereby incorporated by reference in its entirety). In some embodiments, a quality score is a Phred score, which is a log-scaled probability that a base call is incorrect (e.g., as described in Ruffalo et al., 2012, Bioinformatics 28(5):i349-i355).

Such a method provides increased coverage near contig ends (thus enabling better polishing), improved phasing of reads, and improved ability to resolve complex repeat structures in the assembly.

Use Case 2: Phasing Reads Via Mapping to Haplotig Graphs.

A: Phasing Long Reads Using Haplotig Graphs.

Resolving haplotype scaffolds through a combination of FALCON-unzip haplotig assemblies and long-range sequencing data (e.g., 10x, Dovetail, Bionano) is a common procedure used by groups such as the Vertebrate Genome Project (VGP) consortium. Mapping long-range reads should be much more accurate when the context of an assembly graph is available. Unzip assemblies are highly contiguous, but the connectivity information is usually discarded when long-range data is aligned. Often, the short paired-end reads are mapped only to the contigs/haplotigs. In case of slightly repetitive regions (which are abundant on larger genomes), the mapping can become ambiguous. The graph context can constrain the mapping results to one region where there is a path (of acceptable length) between candidate target sequences. A related method uses Hi-C data in combination with GFA-formatted assembly graphs in order to accurately scaffold the assemblies (see Ghurye et al. bioRxiv 261149; on the Internet at doi.org/10.1101/261149).

A further nucleic acid sequencing method is provided that comprises constructing a haplotig assembly graph for a single diploid or polyploid organism of a species having a heterozygous genome. The haplotig assembly graph represents the heterozygous genome and comprises one or more nonlinear topological components (e.g., bubbles or cycles). Each respective nonlinear topological component in the one or more nonlinear topological components has a corresponding initiating node and a corresponding terminal node that are connected by at least a corresponding first branch and a corresponding second branch. The corresponding first and second branch respectively represent a first and second phased haplotig corresponding to a first and second homologous chromosome in the heterozygous genome.

In some embodiments, for example in a polyploid genome, there can be 2 or more branches. In some embodiments, there can be 3 or more branches, 4 or more branches, 5 or more branches, 6 or more branches, 7 or more branches, 8 or more branches, 9 or more branches, or 10 or more branches.

The method continues by obtaining a plurality of sequence reads from a biological sample obtained from the single diploid or polyploid organism in electronic format. A first sequence read in the plurality of sequence reads encompasses at least the corresponding initiating node or the corresponding terminal node of a first nonlinear topological component in the one or more nonlinear topological components. In come embodiments, the method could also encompass both initiating and terminal nodes as well as the entire bubble (or cycles or even multiple nearby bubbles). The method proceeds by using the haplotig assembly graph to form a mapping of each respective sequence read in the plurality of sequence reads. The mapping of the first sequence read is reported as a split alignment comprising (i) a first alignment component to a first portion of the haplotig assembly graph, (ii) a second alignment component to a second portion of the haplotig assembly graph and (iii) a path describing a relation in the haplotig assembly graph between the first portion and the second portion of the haplotig assembly graph, wherein one of the first portion and the second portion is in the first or second branch of the first nonlinear topological component and the other of the first portion and the second portion is not in a branch of the first nonlinear topological component.

In some embodiments, the mapping provides a start position and an end position for the respective sequence read in a target sequence, and wherein the one or more programs singularly or collectively further comprise instructions for aligning the respective sequence read to the target sequence using a sequence alignment algorithm and the start position and the end position.

In some embodiments, the haplotig assembly graph is formed using the plurality of sequence reads by overlapping respective sequence reads in the plurality of sequence reads. An amount of overhang between an overlapped first sequence read and second sequence is unrestricted provided there is a minimum consensus region between the first and second sequence reads. This is distinct from de Bruijn graphs, which have a specific k-mer length overlap for each sequence read. Details of overlap length are discussed above and are not repeated here.

B: Phasing Paired-End Short Sequence Reads Using Haplotig Graphs.

One aspect of the present disclosure provides a nucleic acid sequencing method that comprises constructing a haplotig assembly graph for a single diploid or polyploid organism having a heterozygous genome. The haplotig assembly graph represents the heterozygous genome and comprises one or more nonlinear topological components (bubbles or cycles). Each respective nonlinear topological component in the one or more nonlinear topological components has a corresponding initiating node and a corresponding terminal node that are connected by at least a corresponding first branch and a corresponding second branch. The corresponding first and second branch respectively represent a first and second phased haplotig corresponding to a first and second homologous chromosome in the heterozygous genome.

The method proceeds by obtaining a plurality of paired-end sequence reads from a biological sample obtained from the single diploid or polyploid organism in electronic format. A first set of paired-end sequence reads in the plurality of paired-end sequence reads encompasses at least the corresponding initiating node or the corresponding terminal node of a first nonlinear topological component in the one or more nonlinear topological components (e.g., bubbles or cycles). The method continues by using the haplotig assembly graph to form a mapping of each respective paired-end sequence read in the plurality of paired-end sequence reads. The mapping of the first set of paired-end sequence reads is reported as a split alignment comprising (i) a first alignment component to a first portion of the haplotig assembly graph representing a first sequence read in the first set of paired-end sequence reads, (ii) a second alignment component to a second portion of the haplotig assembly graph representing a second sequence read in the first set of paired-end sequence reads and (iii) a path describing a relation in the haplotig assembly graph between the first portion and the second portion of the haplotig assembly graph. One of the first portion and the second portion is in the first or second branch of the first nonlinear topological component and the other of the first portion and the second portion is not in a branch of the first nonlinear topological component.

In some embodiments, the mapping provides a start position and an end position for each respective set of paired-end sequence reads in a target sequence. The one or more programs singularly or collectively further comprise instructions for aligning each respective set of paired-end sequence reads to the target sequence using a sequence alignment algorithm and the start position and the end position.

In some embodiments, the haplotig assembly graph is formed using the plurality of paired-end sequence reads by overlapping respective paired-end sequence read sets in the plurality of paired-end sequence reads. An amount of overhang between an overlapped first set of paired-end sequence read set and a second set of paired-end sequence read sets is unrestricted provided there is a minimum consensus region between the first set of paired-end sequence read set and the second set of paired-end sequence read sets.

In some embodiments, the minimum consensus region comprises at least 1 base, at least 2 bases, at least 3 bases, at least 4 bases, at least 5 bases, at least 6 bases, at least 7 bases, at least 8 bases, at least at least 9 bases, at least 10 bases, at least 15 bases, at least 20 bases, at least 30 bases, at least 40 bases, at least 50 bases, at least 60 bases, at least 70 bases, at least 80 bases, at least 90 bases, at least 100 bases, at least 500 bases, or at least 1000 bases. In some embodiments, each consensus region has the same overlap length. In some embodiments, each consensus region has a different overlap length. In some embodiments, a first set of consensus regions have a first overlap length and a second set of consensus regions have a second overlap length.

Figure 4A:
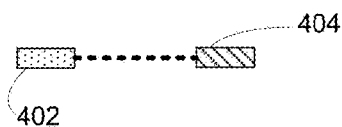
FIGS. 4A, 4B, and 4C collectively illustrate example graphs in accordance with some embodiments of the present disclosure.
Figure 4B:
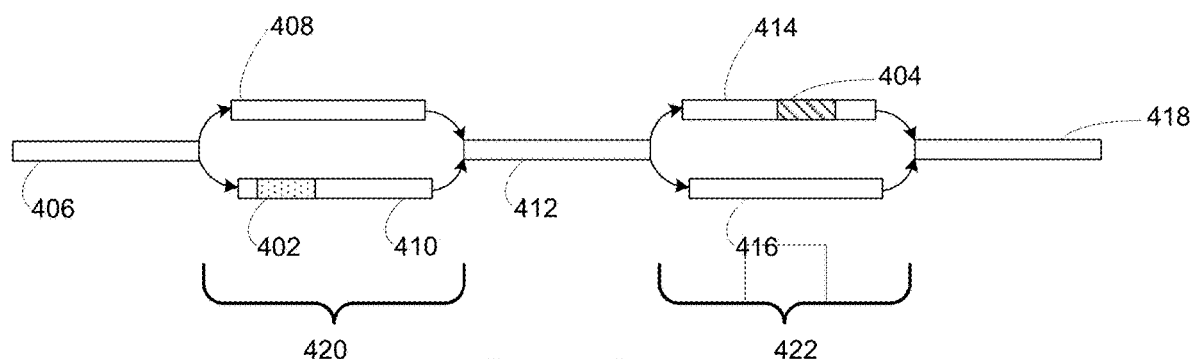
Figure 4C:
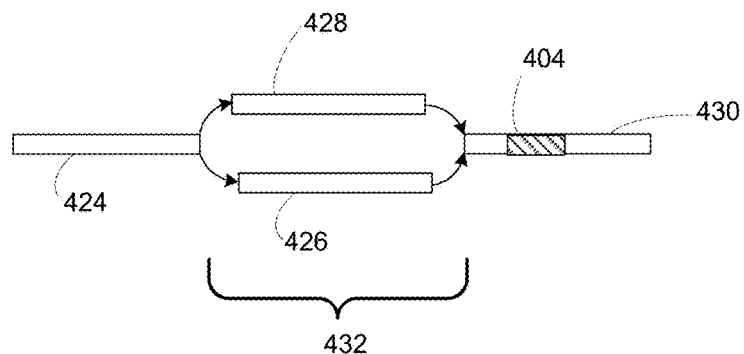

As illustrated in FIGS. 4A, 4B, and 4C, the haplotig assembly graph may comprise one or more bubbles (e.g., 420, 422, and 432) representing phased haplotigs. The regions between each phase haplotig (e.g., 406, 412, and 418) are typically collapsed sequences that do not contain sufficient information to be successfully phased.

Once an assembly is unzipped (e.g., using FALCON-unzip), a haplotig graph is available as an intermediate output. In some embodiments, the haplotig graph is a Directed Acyclic Graph (DAG), composed of bubbles with at least two branches (one for each haplotype) and collapsed regions (e.g., regions in the genome where there was not enough information to perform phasing). Bubble branches in each graph (e.g., 420, 422) represent phased portions of a diploid genome. Reads can be mapped to the FALCON-unzip haplotig graph and phased by selecting a branch in the graph with the highest alignment score as the most likely destination (e.g., phase).

FIGS. 4B and 4C illustrate two possible graphs of the same assembly, and a potential mapping of two long-range paired-end reads 402 and 404. In some embodiments, the orientation of the two paired-end reads 402 and 404 is known. In such embodiments, it is possible to determine the graph illustrated in FIG. 4B, where the locations of each bubble 420 and 422 are known in regards to each other. In some embodiments, due to the connectivity information provided by the known locations of 402 and 404, the first mapping location is potentially preferred. In some embodiments, the connectivity between 402 and 404 is not known, and thus only each individual bubble 420 and 422 are determined. In some embodiments, read 404 is repetitive and is also mapped to a second graph location (e.g., on region 430 in FIG. 4C).

In some embodiments, the method serves to improve outcomes in resolving haplotype scaffolds, provides higher quality assemblies, and improve FALCON unzip results.

Use Case 3: Mapping to Circular Genomes.

Circular genomes can be modeled in a graph context, by simply adding a single edge linking the end of a chromosome to the beginning of the same chromosome. A graph-aware mapper would in this case know that the alignment can safely be extended after the sequence ends, and continue from its own beginning. Specifying circular context via a graph definition allows for a mixed reference of linear and circular chromosomes in the input FASTA sequence set (e.g., a eukaryotic genome).

Accordingly, one aspect of the present disclosure provides a nucleic acid sequencing method in which a graph for a species having a circular genome is obtained. The graph represents the circular genome and comprises a segment line specifying a sequence of the circular genome. A beginning of the sequence defines a beginning of the segment line and an end of the sequence defines an end of the segment line, and an edge line representing a circular border in the graph, the edge line specifying that the end of the segment line is linked to the beginning of the segment line. The method continues with obtaining a plurality of sequence reads from a biological sample obtained from an organism of the species in electronic format. A first sequence read in the plurality of sequencing reads spans the circular border. The method proceeds by using the graph to form a mapping of each sequencing read in the plurality of sequencing reads. The mapping of the first sequencing read is reported as a split alignment comprising (i) a first alignment component to a terminal portion of the sequence, (ii) a second alignment component to an initial portion of the sequence, and (iii) a path describing a relation in the graph between the terminal portion of the sequence and the initial portion of the sequence in the graph.

Another aspect of the present disclosure provides a nucleic acid sequencing method in which a graph for a species having a circular genome is obtained. The graph represents the circular genome and comprises a segment line specifying a sequence of the circular genome. A beginning of the sequence defines a beginning of the segment line and an end of the sequence defines an end of the segment line. An edge line representing a circular border in the graph, the edge line specifying that the end of the segment line is linked to the beginning of the segment line. The method continues by obtaining a plurality of paired-end sequencing reads from a biological sample obtained from an organism of the species in electronic format. A first set of paired-end sequencing reads in the plurality of paired-end sequencing reads encompasses the circular border. The method proceeds by using the graph to form a mapping of each paired-end sequencing read in the plurality of paired-end sequence reads. The mapping of the first set of paired-end sequence reads is reported as a split alignment comprising (i) an alignment of a first sequence read in the first set of paired-end sequence reads to a terminal portion of the sequence, (ii) an alignment of a second sequence read in the first set of paired-end sequence reads to an initial portion of the sequence, and (iii) a path describing a relation in the graph between the terminal portion and the initial portion of the graph.

Figure 5:
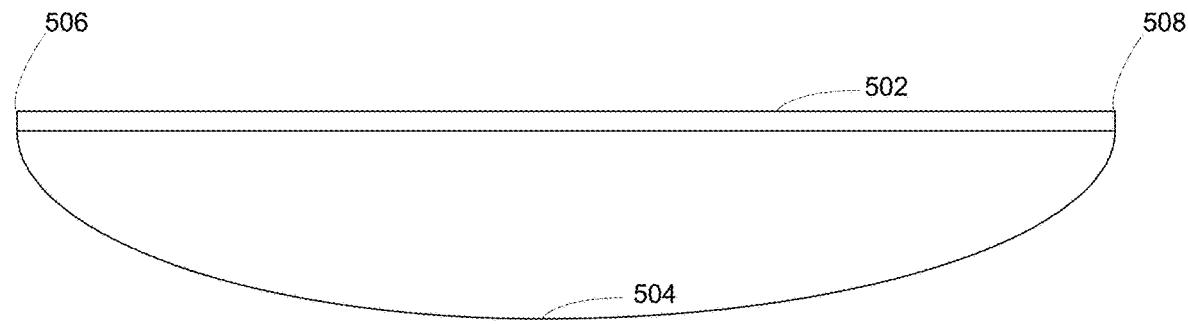
FIG. 5 illustrates an example of mapping to a circular genome, in accordance with some embodiments of the present disclosure.

FIG. 5 illustrates a circular reference genome. A circular reference is the simplest form of a graph, with only one edge 504 linking the end of the sequence 508 to its beginning 506. A graph-based mapper can detect reads which should be aligned across the gap and construct the correct alignment. This ensures that the high coverage of mapped reads is retained at the front and the back of such contigs, which in turn enables better polishing of circular contigs. In some embodiments, the FALCON assembler contains a feature to output the circular edges for circular contigs natively. This means that, should a graph-based mapper be used with such a contig graph, Arrow or other polishing tools would have an almost uniform coverage of reads available at their disposal (which is currently an issue when using BLASR as the default aligner).

In some embodiments, reads that span the circular border will have two mapping locations reported. In some embodiments, a first mapping location occurs near the beginning 506 of the chromosome 502, reaching as far as the end 508. In some embodiments, a second mapping location occurs near the end 508 of the chromosome, ideally reaching as far as the beginning 506. In some additional embodiments, a mapping path is provided to describe the relationship between the first and the second mappings. This method ensures good coverage of mapped reads across the circular genome and allows for much better polishing of the sequences.

Use Case 4: Mapping with Genomic Inversions.

Inversions occur as natural structural variations (SVs) between different genomes. Many current mappers do not perform well with sequences containing inversions. For example, Chen et al. describe the structural variation predictions of a variety of mapping tools, and every method analyzed had a comparatively low success rate with inversions (Nat Methods 6(9):677-681, 2009). The detection of inversions seamlessly emerges from the definition of graph-based mapping as described herein. In some embodiments of the present disclosure, a portion of the sequence that maps to the reverse-complement strand of the reference can be linked to the rest of the query fragments via implicit edges.

Accordingly, one aspect of the present disclosure provides a nucleic acid sequencing method in which a query sequence representing a portion of a genomic sequence of an organism of a species comprising genomic inversions is obtained in electronic format. The query sequence comprises a first query portion and a second query portion. In the method, the query sequence is mapped to a target sequence for the species. The mapping includes mapping the first query portion to a first target portion of a first strand of the target sequence and mapping the second query portion to a second target portion of a second strand of the target sequence, where the first strand is the reverse complement of the second strand thereby forming a split alignment comprising (i) a first alignment component comprising an alignment of the first query portion to the first target portion of the first strand, (ii) a second alignment component comprising an alignment of the second query portion to the second target portion of the second strand, and (iii) an alignment path describing a relation between the first target portion and the second target portion.

In some embodiments, the query sequence comprises a third query portion. In some embodiments, the query sequence comprises a fourth query portion, a fifth query portion, a sixth query portion, a seventh query portion, an eighth query portion, a ninth query portion, or a tenth query portion. In some embodiments, there can be multiple inversions in the same query. In some embodiments, one query can include 1 or more inversions, 2 or more inversions, 3 or more inversions, 4 or more inversions, 5 or more inversions, 10 or more inversions, 15 or more inversions, or 20 or more inversions.

The mapping includes mapping the third query portion to a third reference portion of the first strand and the split alignment further comprises a third alignment component comprising an alignment of the third query portion to the third reference portion of the first strand and the alignment path further describes a relation of the first reference portion and the second reference portion to the third reference portion.

In some embodiments, the query sequence is a single sequence read obtained from a biological sample of the organism. In some embodiments, the query sequence is a contig formed from a plurality of sequence reads obtained from a biological sample of the organism.

Figure 6A:
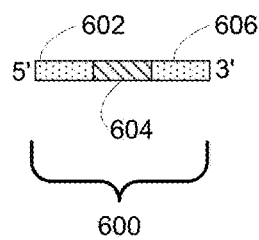
FIGS. 6A and 6B collectively illustrate an example of mapping with genomic inversions, in accordance with some embodiments of the present disclosure.
Figure 6B:
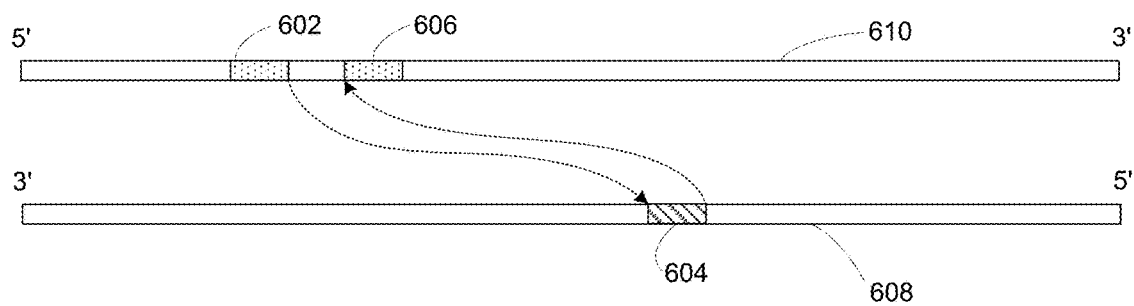

FIGS. 6A and 6B illustrate an example of inversion mapping. A query sequence 600 has one or more anchors to the reference genome. As shown in FIG. 6A, in some embodiments, query sequence 600 comprises three anchor sequences 602, 604, and 606.

In some embodiments, a query sequence comprises at least 2 anchor sequences, at least 3 anchor sequences, at least 4 anchor sequences, at least 5 anchor sequences, at least 6 anchor sequences, at least 7 anchor sequences, at least 8 anchor sequences, at least 9 anchor sequences, or at least 10 anchor sequences.

As shown in FIG. 6B, two of the anchor sequences 602 and 606 map to the forward strand 610 of the reference sequence, and the third anchor sequence 604 maps to the corresponding reverse strand 608 of the reference sequence. Unlike what is described for other use cases herein, the graph for this embodiment cannot be predetermined via a reference sequence or other input. Rather, in this embodiment, the graph is determined implicitly. In some embodiments, a graph determined by this method is subsequently analyzed for structural variants.

Use Case 5: Modeling a SMRTbell™ Reference as a Graph.

In some embodiments, a SMRTbell template is used. As described by Travers et al., in some embodiments, a SMRTbell template is composed of a sequence of interest, adapter sequences, and optionally barcode sequences (Nucleic Acids Res 38(15):e159, 2010). In some embodiments, a known region of a genome is targeted for sequencing. In such embodiments, a closely related reference sequence is used to model the insert and construct a circular graph. In some embodiments, using a SMRTbell template improves sequencing efficiency, as the adapter and/or barcode sequences facilitate aligning an unrolled long-read sequence (e.g., a long-read sequence that has traversed the circular template more than once). In some embodiments, a long-read sequence traverses the circular template at least 1 time, at least 2 times, at least 5 times, at least 10 times, at least 20 times, or at least 50 times.

In one aspect in accordance with Use Case 5, a nucleic acid sequencing method is provided that includes obtaining a circular graph. The circular graph comprises a first segment specifying an insert sequence in a first direction, a second segment specifying an adapter sequence in a first direction, a third segment specifying the insert sequence in a second direction, a fourth segment specifying the adapter sequence in a second direction, a first edge connecting an end of the first segment to a beginning of the second segment, a second edge connecting an end of the second segment to a beginning of the third segment, a third edge connecting an end of the third segment to a beginning of the fourth segment, and a fourth edge connecting an end of the fourth segment to a beginning of the first segment. The second direction is the reverse complement of the first direction.

The method proceeds by obtaining a sequence read from a biological sample in electronic format. The sequence read spans a sequence represented by the circular graph. The method then continues by using the graph to form a mapping of the sequence read. The mapping of the sequence read is reported as an alignment of each instance of the insert sequence in the sequence read.

In some embodiments, the mapping further comprises an alignment of each instance of the adapter sequence.

In some embodiments, the sequence read spans the circular graph a plurality of times. In some embodiments, the plurality of times is three or more times. In some embodiments, the plurality of times is five or more times. In some embodiments, the plurality of times is twenty or more times.

Figure 7A:
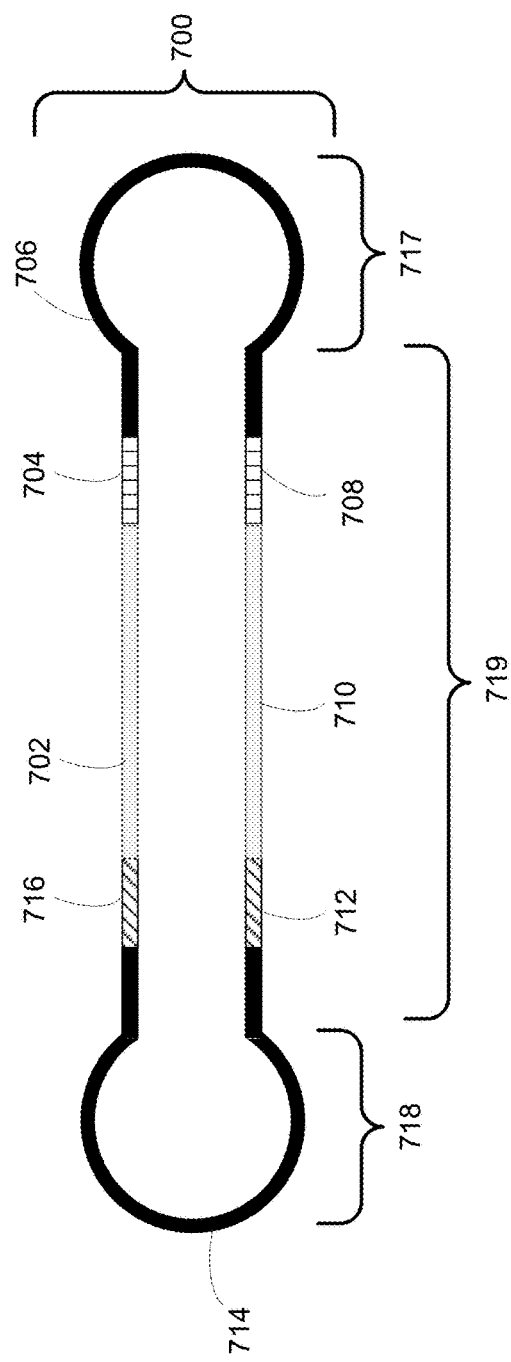
FIGS. 7A and 7B collectively illustrate an example of using a known insert sequence for mapping (such as a plasmid, mitochondrial DNA, or targeted genomic region), in accordance with some embodiments of the present disclosure.

A SMRTbell™ construct, for example as illustrated in FIG. 7A, is composed of the desired insert to sequence (e.g., 702, and 710), adapters (e.g., 706 and 714), and optionally, barcode sequences (e.g., 704, 708, 712, and 716). In some embodiments, a known region of a genome is targeted for sequencing, and a closely related reference sequence is used to model the insert and construct a circular graph from the circular construct. In some embodiments, the barcode sequences are reverse complements of each other (e.g., the pairs of 712/716 and 704/708). In some embodiments, the barcode sequences are symmetric (e.g., 716 will be the reverse complement of 708 or 712). In some embodiments, the barcode sequences are not symmetric (e.g., 716 is not the reverse complement of 708 or 712). In some embodiments, the desired insert will be present in both a forward (e.g., 702) and a reverse (e.g., 710) sequence. In some embodiments, one or more regions of the circular construct is double stranded (e.g., 719). In some embodiments, the adaptor sequences (e.g., 714 and 706) are reverse complements of each other. In some embodiments, the adaptor sequences (e.g., 714 and 706) are not reverse complements of each other. In some embodiments, each adaptor sequence forms a hairpin region at each end of the circular construct (e.g., 718 and 717).

In some embodiments of the present disclosure, unrolling and aligning a ZMW read along a known amplicon reference is modelled in a graph context. In the simplest case (e.g., without the optional barcode sequences 704, 708, 712, and 716) a graph based on the circular construct would comprise a first segment (e.g., 714), a second segment (e.g., 702), a third segment (e.g., 706), a fourth segment (e.g., 710), and an edge between every two of these segments. In some embodiments, two of the segments will be reverse complements of each other (e.g., 702 and 710).

Figure 7B:
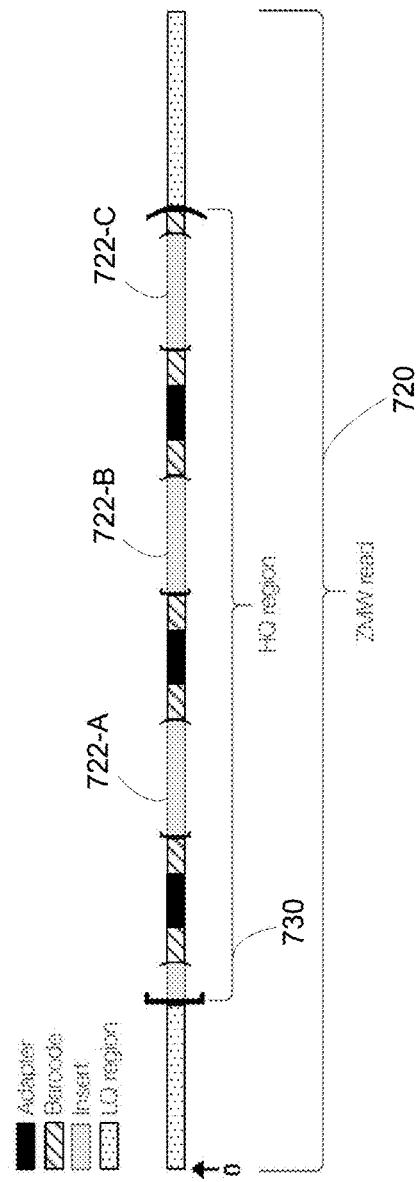

In some embodiments, a sequencing read from the SMRTbell™ construct comprises a ZMW read 720, as illustrated in FIG. 7B. As can be seen in FIG. 7B, in some embodiments—depending on how long the ZMW read is—multiple copies of the insert sequence (e.g., 722-A, 722-B, and 722-C) will be present. In some embodiments, each copy of the insert sequence is known as a subread, and the multiple subreads are compared to each other, thus improving the accuracy of the overall sequencing result.

Use Case 6: Transcriptome Mapping Via Edges that Define Splice Sites.

Transcriptome mapping is a natural application for a graph-based mapper. Accordingly, in some embodiments, the disclosed methods address circRNA mapping. CircRNAs are circular molecules. Sequencing of such circular molecules, in some embodiments, produces exons that appear to be out of order but are actually a circular permutation of the spliced exons. In some embodiments, adding a circular edge to the transcriptome enables mapping of such RNA-seq data. An example of circRNA mapping is described by Li et al., but that method depends on k-mer analysis and would not work with the long sequence reads used in the present disclosure (BMC Genomics 19(Suppl 6):572, 2018).

Accordingly, a method in accordance with Use Case 6 provides a nucleic acid sequencing method that comprises obtaining a transcriptome annotation that defines a mapping of each respective exon in a plurality of exons in a reference sequence for a species, and constructing a graph corresponding to the transcriptome annotation. The graph comprises the reference sequence for the species, a first segment, a second segment, and a link between the 3' end of the first exon and the 5' end of the second exon.

In some embodiments, the first segment represents a first exon in the plurality of exons. In some embodiments, exons are sequences represented as nodes in the graph. In some embodiments, edges represent the splice sites (e.g., those locations where two segments are virtually joined together). In some embodiments, the first segment further includes respective coordinates of the 5' end and the 3' end of the first exon in the reference sequence. In some embodiments, the second segment represents a second exon in the plurality of exons and includes respective coordinates of the 5' end and the 3' end of the second exon in the reference sequence.

FIGS. 8A and 8B illustrate an example of transcriptome mapping. In some embodiments, transcriptomes are described by graphs marking the splicing regions along a reference genome (e.g., 810). The first segment (e.g., an individual node or a set of nodes) represents a first exon 802 in the plurality of exons (e.g., 802, 804, 806, and 808). In some embodiments, exons as sequences are represented as the nodes, or sets of nodes, in the graph. Edges represent the splice sites where two segments should be virtually joined together. The first segment further includes respective coordinates of the 5' end and the 3' end of the first exon in the reference sequence. The second segment represents a second exon in the plurality of exons, and includes respective coordinates of the 5' end and the 3' end of the second exon in the reference sequence.

The method proceeds by obtaining a sequence read of an mRNA from a biological sample of an organism of the species in electronic format. The sequence read comprises the first exon and the second exon (e.g., 802 and 804). In some embodiments, the sequence read comprises at least 2 exons, at least 3 exons, at least 4 exons, at least 5 exons, at least 6 exons, at least 7 exons, at least 8 exons, at least 9 exons, or at least 10 exons. The method then continues by using the graph to form a mapping of the sequence read to the reference sequence 810.

In some embodiments, the links allow the mapping to proceed even when the order of exons in the sequence read is not the same as the linear order they appear in the reference genome. In some embodiments, a third exon not in the sequence read intervenes between the first exon and the second exon in the reference sequence.

In some embodiments, the query sequence is obtained from circular RNA molecules (circRNA), and the order of exons in the query sequence is not linear with their respective order in the reference sequence.

Transcriptome annotations can be represented in the form of a graph, linking neighboring splice sites. With the application of a graph-based mapper, the transcriptome sequence does not need to be explicitly constructed prior to mapping Isoseq/RNA-seq reads.

In some embodiments, the expected result of transcriptome mapping is a spliced alignment with either a predefined number of CIGAR (Concise Idiosyncratic Gapped Alignment Report) operations within the same alignment, or an alignment path of individual exon regions along the genome. In some embodiments, the set of possible CIGAR operations includes at least an alignment match (e.g., either a sequence match or mismatch), an insertion to the reference, a deletion from the reference, a region skipped from the reference, a sequence match, or a sequence mismatch.

CONCLUSION

Plural instances may be provided for components, operations or structures described herein as a single instance. Finally, boundaries between various components, operations, and data stores are somewhat arbitrary, and particular operations are illustrated in the context of specific illustrative configurations. Other allocations of functionality are envisioned and may fall within the scope of the implementation(s). In general, structures and functionality presented as separate components in the example configurations may be implemented as a combined structure or component. Similarly, structures and functionality presented as a single component may be implemented as separate components. These other variations, modifications, additions, and improvements fall within the scope of the implementation(s).

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting (the stated condition or event (" or "in response to detecting (the stated condition or event)," depending on the context.

The foregoing description included example systems, methods, techniques, instruction sequences, and computing machine program products that embody illustrative implementations. For purposes of explanation, numerous specific details were set forth in order to provide an understanding of various implementations of the inventive subject matter. It will be evident, however, to those skilled in the art that implementations of the inventive subject matter may be practiced without these specific details. In general, wellknown instruction instances, protocols, structures and techniques have not been shown in detail.

The foregoing description, for purpose of explanation, has been described with reference to specific implementations. However, the illustrative discussions above are not intended to be exhaustive or to limit the implementations to the precise forms disclosed. Many modifications and variations are possible in view of the above teachings. The implementations were chosen and described in order to best explain the principles and their practical applications, to thereby enable others skilled in the art to best utilize the implementations and various implementations with various modifications as are suited to the particular use contemplated.

What is claimed is:

1. A method for assembling long sequence reads to determine the sequence of a nucleic acid, comprising:
    at a computer system comprising one or more processors and a memory, the memory storing one or more programs, the one or more programs singularly or collectively comprising instructions for:
    obtaining a directed graph for a single diploid or polyploid organism of a species having a heterozygous genome, wherein the directed graph represents all or a portion of the heterozygous genome and comprises one or more nonlinear topological components, wherein each respective nonlinear topological component in the one or more nonlinear topological components represents a variation with respect to a set of target sequences, each respective nonlinear topological component in the one or more nonlinear topological components has a corresponding initiating node and a corresponding terminal node that are connected by at least a corresponding first branch and a corresponding second branch, wherein one of the corresponding first branch and the corresponding second branch corresponds to a target sequence in the set of target sequences, and the directed graph is formed using a plurality of sequence reads from a biological sample of the single organism, which collectively have random error with respect to a target sequence in the set of target sequences that is greater than ten percent, by overlapping respective sequence reads in the plurality of sequence reads, wherein an amount of overhang between an overlapped first sequence read and second sequence is unrestricted provided there is a minimum consensus region between the first and second sequence reads;

obtaining a query sequence from the biological sample in electronic format, wherein the query sequence is either (i) a sequence read in the plurality of sequence reads, or (ii) a scaffold formed from the plurality of sequence reads, wherein the query sequence encompasses at least the corresponding initiating node or the corresponding terminal node of a first nonlinear topological component in the one or more nonlinear topological components;

using the directed graph to form a mapping of the query sequence to the directed graph, wherein the mapping of the query sequence comprises (i) a first alignment component to a first portion of the directed graph, (ii) a second alignment component to a second portion of the directed graph and (iii) a path describing a relation in the directed graph between the first portion and the second portion of the directed graph, wherein one of the first portion and the second portion is in the first or second branch of the first nonlinear topological component and the other of the first portion and the second portion is not in a branch of the first nonlinear topological component; and using the mapping to determine the nucleic acid sequence of the query sequence.

2. The nucleic acid sequencing method of claim 1, wherein the corresponding first and second branch of a nonlinear topological component in the one or more nonlinear topological components respectively represent a first allele and a second allele for a variation in the heterozygous genome.

3. The nucleic acid sequencing method of claim 1, wherein the query sequence is a sequence read in the plurality of sequence reads.

4. The nucleic acid sequencing method of claim 1, wherein the query sequence is a scaffold formed from a consensus of two or more sequence reads in the plurality of sequence reads.

5. The nucleic acid sequencing method of claim 1, wherein the plurality of sequence reads has an average sequence length of greater than 10,000 base pairs.

6. The nucleic acid sequencing method of claim 1, wherein the mapping provides a start position and an end position in the target sequence for the query sequence, and wherein the one or more programs singularly or collectively further comprise instructions for aligning the query sequence to the target sequence using a sequence alignment algorithm and the start position and the end position.

7. The nucleic acid sequencing method of claim 1, wherein the sequence alignment algorithm is a dynamic programming global alignment algorithm, a dynamic programming semi-global alignment algorithm, or a dynamic programming local alignment algorithm.

8. The nucleic acid sequencing method of claim 1, wherein
the directed graph represents at least ten percent of the heterozygous genome, and
the directed graph comprises ten or more nonlinear topological components.

9. The nucleic acid sequencing method of claim 1, wherein
the directed graph represents at least fifty percent of the heterozygous genome, and
the directed graph comprises twenty-five or more nonlinear topological components.

10. The nucleic acid sequencing method of claim 1, wherein the directed graph comprises at least 500,000 nodes.

11. The nucleic acid sequencing method of claim 1, wherein the directed graph comprises at least 100,000 nonlinear topological components.

12. An executable software product stored on a computer-readable medium containing program instructions for assembling long sequence reads to determine the sequence of a nucleic acid, the program instructions executing on at least one processor, comprising:

obtaining a directed graph for a single diploid or polyploid organism of a species having a heterozygous genome, wherein the directed graph represents all or a portion of the heterozygous genome and comprises one or more nonlinear topological components, wherein each respective nonlinear topological component in the one or more nonlinear topological components represents a variation with respect to a set of target sequences, each respective nonlinear topological component in the one or more nonlinear topological components has a corresponding initiating node and a corresponding terminal node that are connected by at least a corresponding first branch and a corresponding second branch, wherein one of the corresponding first branch and the corresponding second branch corresponds to a target sequence in the set of target sequences, and the directed graph is formed using a plurality of sequence reads from a biological sample of the single organism, which collectively have random error with respect to a target sequence in the set of target sequences that is greater than ten percent, by overlapping respective sequence reads in the plurality of sequence reads, wherein an amount of overhang between an overlapped first sequence read and second sequence is unrestricted provided there is a minimum consensus region between the first and second sequence reads;

obtaining a query sequence from the biological sample in electronic format, wherein the query sequence is either (i) a sequence read in the plurality of sequence reads, or (ii) a scaffold formed from the plurality of sequence reads, wherein the query sequence encompasses at least the corresponding initiating node or the corresponding terminal node of a first nonlinear topological component in the one or more nonlinear topological components;

using the directed graph to form a mapping of the query sequence to the directed graph, wherein the mapping of the query sequence comprises (i) a first alignment component to a first portion of the directed graph, (ii) a second alignment component to a second portion of the directed graph and (iii) a path describing a relation in the directed graph between the first portion and the second portion of the directed graph, wherein one of the first portion and the second portion is in the first or second branch of the first nonlinear topological component and the other of the first portion and the second portion is not in a branch of the first nonlinear topological component; and using the mapping to determine the nucleic acid sequence of the query sequence.

13. A system for assembling long sequence reads to determine the sequence of a nucleic acid, comprising:

a memory; and a processor coupled to the memory configured to:

obtain a directed graph for a single diploid or polyploid organism of a species having a heterozygous genome, wherein the directed graph represents all or a portion of the heterozygous genome and comprises one or more nonlinear topological components, wherein each respective nonlinear topological component in the one or more nonlinear topological components represents a variation with respect to a set of target sequences, each respective nonlinear topological component in the one or more nonlinear topological components has a corresponding initiating node and a corresponding terminal node that are connected by at least a corresponding first branch and a corresponding second branch, wherein one of the corresponding first branch and the corresponding second branch corresponds to a target sequence in the set of target sequences, and the directed graph is formed using a plurality of sequence reads from a biological sample of the single organism, which collectively have random error with respect to a target sequence in the set of target sequences that is greater than ten percent, by overlapping respective sequence reads in the plurality of sequence reads, wherein an amount of overhang between an overlapped first sequence read and second sequence is unrestricted provided there is a minimum consensus region between the first and second sequence reads;

obtain a query sequence from the biological sample in electronic format, wherein the query sequence is either (i) a sequence read in the plurality of sequence reads, or (ii) a scaffold formed from the plurality of sequence reads, wherein the query sequence encompasses at least the corresponding initiating node or the corresponding terminal node of a first nonlinear topological component in the one or more nonlinear topological components;

use the directed graph to form a mapping of the query sequence to the directed graph, wherein the mapping of the query sequence comprises (i) a first alignment component to a first portion of the directed graph, (ii) a second alignment component to a second portion of the directed graph and (iii) a path describing a relation in the directed graph between the first portion and the second portion of the directed graph, wherein one of the first portion and the second portion is in the first or second branch of the first nonlinear topological component and the other of the first portion and the second portion is not in a branch of the first nonlinear topological component; and use the mapping to determine the nucleic acid sequence of the query sequence.

* * * * *